(12) United States Patent
Court et al.

(10) Patent No.: US 11,951,295 B2
(45) Date of Patent: Apr. 9, 2024

(54) APPARATUS FOR EXTRACORPOREAL BLOOD TREATMENT

(71) Applicant: GAMBRO LUNDIA AB, Lund (SE)

(72) Inventors: Thierry Court, Villeurbanne (FR); Dominique Pouchoulin, Tramoyes (FR)

(73) Assignee: Gambro Lundia AB, Lund (SE)

( * ) Notice: Subject to any disclaimer, the term of this patent is extended or adjusted under 35 U.S.C. 154(b) by 955 days.

(21) Appl. No.: 16/957,889

(22) PCT Filed: Dec. 21, 2018

(86) PCT No.: PCT/EP2018/086631
§ 371 (c)(1),
(2) Date: Jun. 25, 2020

(87) PCT Pub. No.: WO2019/129719
PCT Pub. Date: Jul. 4, 2019

(65) Prior Publication Data
US 2021/0023283 A1    Jan. 28, 2021

(30) Foreign Application Priority Data
Dec. 29, 2017    (EP) ..................... 17211159

(51) Int. Cl.
*A61M 1/36*    (2006.01)
*A61M 1/34*    (2006.01)
*A61M 60/113*    (2021.01)

(52) U.S. Cl.
CPC ........ *A61M 60/113* (2021.01); *A61M 1/3431* (2014.02); *A61M 1/3607* (2014.02);
(Continued)

(58) Field of Classification Search
CPC .............. A61M 1/3649; A61M 1/3646; A61M 1/3431; A61M 60/113
See application file for complete search history.

(56) References Cited

U.S. PATENT DOCUMENTS 5,114,580 A    5/1992    Ahmad
5,529,685 A    6/1996    Irie
(Continued)

FOREIGN PATENT DOCUMENTS

CN    104968376    10/2015
CN    107296989    10/2017
(Continued)

OTHER PUBLICATIONS

Office Action issued in China for Application No. 201880084801.7 dated Apr. 17, 2023 (23 pages). English translation included.
(Continued)

*Primary Examiner* — Deanna K Hall
(74) *Attorney, Agent, or Firm* — Mueting Raasch Group

(57) ABSTRACT

An apparatus (1) for CRRT is provided comprising a blood circuit (10, 20, 30, 60) with a blood removal line (20), a treatment unit (10), and a blood return line (30). A replacement fluid container (78) is configured for containing a medical fluid, a pre-infusion line (70) has a first end (70-1) connected to the replacement fluid container (78) and a second end (70-2) connected to the blood removal line (20) and a blood pump (22) is active on the blood circuit. A replacement fluid pump (72) is active on the pre-infusion line (70), a dialysate circuit (40, 50, 70) comprises an effluent line (50) configured for discharging fluid from the second chamber, and a control unit (80) is connected to the replacement fluid pump (72) and to the blood pump (22) and is configured for performing a rinse-back procedure for restituting blood to a patient. The rinse-back procedure comprises conveying blood contained in the blood circuit (10, 20, 30, 60) towards the second end (30-2) of the blood return line (30) using the medical fluid.

41 Claims, 14 Drawing Sheets

(52) U.S. Cl.
CPC ........ *A61M 1/3623* (2022.05); *A61M 1/3626* (2013.01); *A61M 1/3646* (2014.02); *A61M 1/3649* (2014.02); *A61M 1/365* (2014.02); *A61M 1/3627* (2013.01)

(56) References Cited

U.S. PATENT DOCUMENTS

| | | | |
|---|---|---|---|
| 6,554,789 | B1 | 4/2003 | Brugger |
| 6,579,253 | B1 | 6/2003 | Burbank |
| 6,638,477 | B1 | 10/2003 | Treu |
| 6,824,524 | B1 | 11/2004 | Favre |
| 6,830,553 | B1 | 12/2004 | Burbank |
| 7,488,301 | B2 | 2/2009 | Beden |
| 9,089,639 | B2 | 7/2015 | Breuel |
| 10,493,196 | B2 | 12/2019 | Riemenschneider |
| 10,561,776 | B2 | 2/2020 | Meyer |
| 2002/0103453 | A1 | 8/2002 | Burbank |
| 2006/0079826 | A1* | 4/2006 | Beden .............. A61M 1/36224 604/4.01 |
| 2007/0161941 | A1 | 7/2007 | Ash |
| 2011/0272337 | A1 | 11/2011 | Palmer |
| 2012/0000547 | A1 | 1/2012 | Gronau |
| 2013/0030346 | A1 | 1/2013 | Gronau |
| 2014/0190887 | A1* | 7/2014 | Rohde .................. B01D 65/02 210/636 |

FOREIGN PATENT DOCUMENTS

| | | |
|---|---|---|
| DE | 10011208 | 9/2001 |
| EP | 2361643 | 8/2011 |
| EP | 2752210 | 7/2014 |
| JP | H06-261938 | 9/1994 |
| JP | 2004313522 | 11/2004 |
| JP | 2005087610 | 4/2005 |
| JP | 2005-537900 | 12/2005 |
| JP | 2009131412 | 6/2009 |
| JP | 2010004905 | 1/2010 |
| JP | 2010004906 | 1/2010 |
| JP | 2010269050 | 12/2010 |
| JP | 2012095843 | 5/2012 |
| JP | 5160975 | 12/2012 |
| JP | 2014-513990 | 9/2014 |
| JP | 2015092977 | 5/2015 |
| JP | 2017-099441 | 6/2017 |
| WO | WO 09/015631 | 12/1990 |
| WO | WO 01/37895 | 5/2001 |
| WO | WO 01/41832 | 6/2001 |
| WO | WO 01/42758 | 6/2001 |
| WO | WO 01/47576 | 7/2001 |
| WO | WO 04/069311 | 8/2004 |
| WO | WO 2008/106191 | 9/2008 |
| WO | WO 2011/140268 | 11/2011 |
| WO | WO 2014/097210 | 6/2014 |
| WO | WO-2014097210 A1 * | 6/2014 .......... A61M 1/3643 |
| WO | WO 2014/110004 | 7/2014 |

OTHER PUBLICATIONS

International Search Report and Written Opinion for PCT/EP2018/086631 dated Feb. 28, 2019 (14 pages).

European Extended Search Report for Application No. 17211159.3 dated Jul. 9, 2018 (7 pages).

* cited by examiner

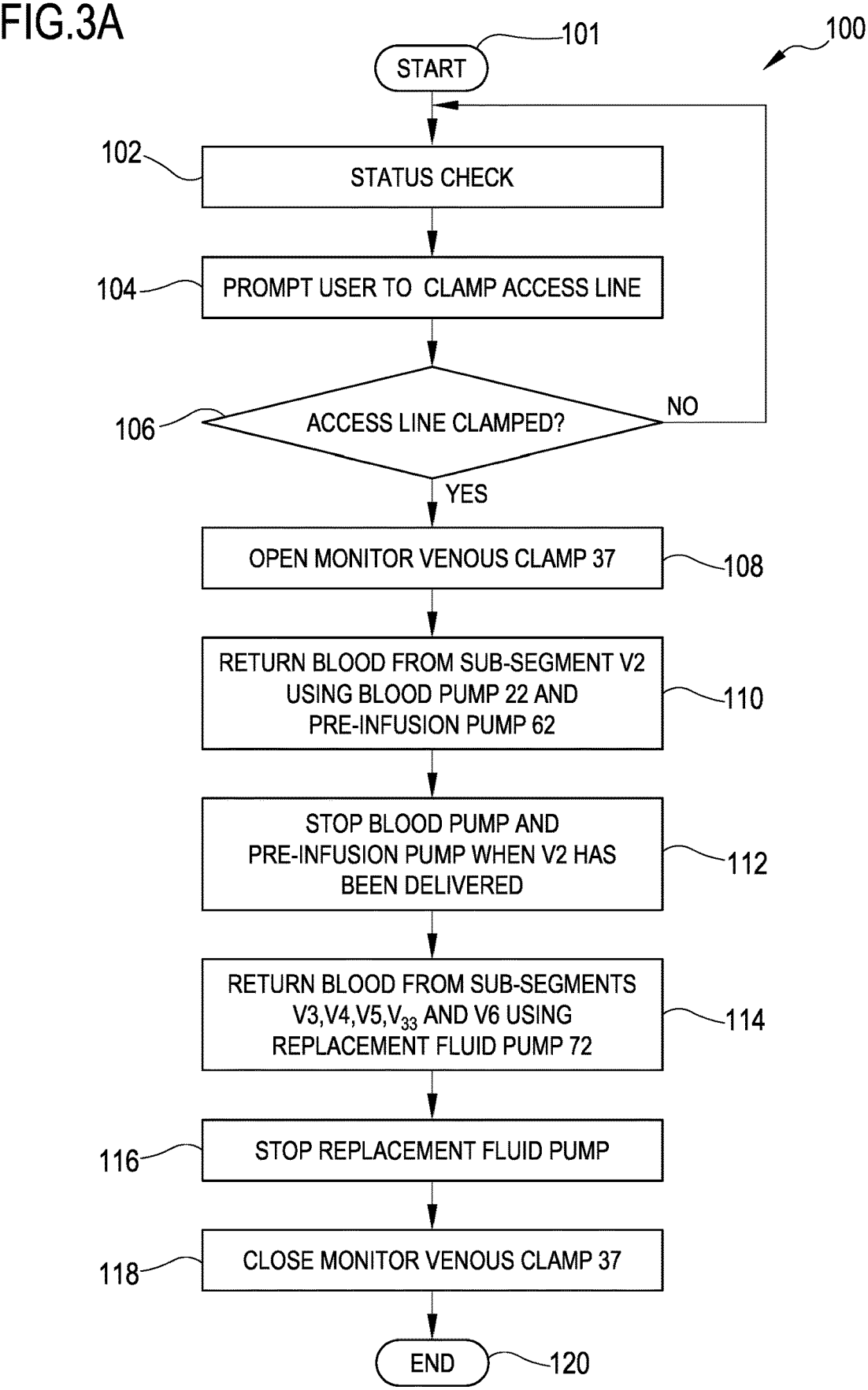

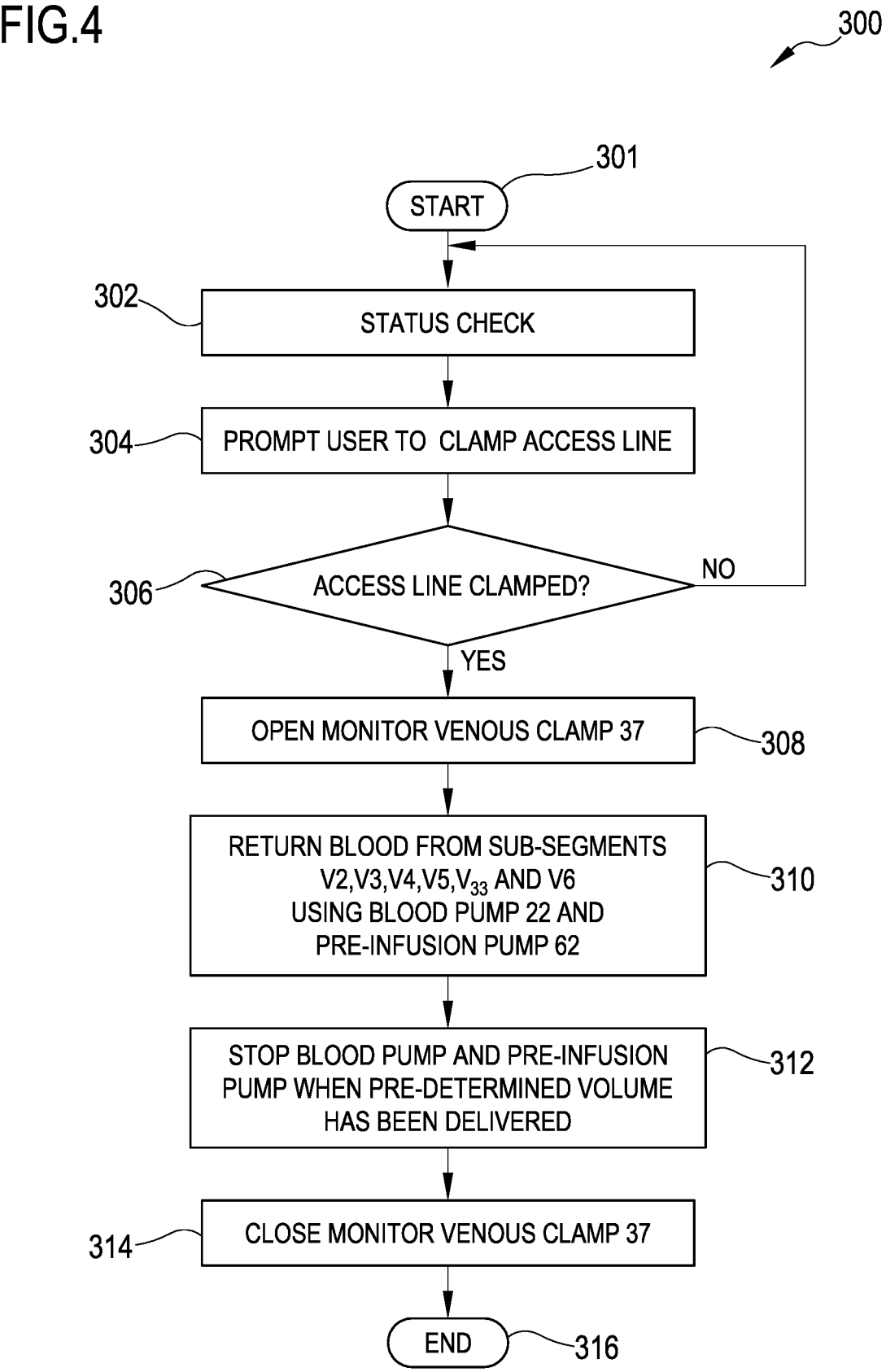

APPARATUS FOR EXTRACORPOREAL BLOOD TREATMENT

This application is a U.S. National Stage Application of International Application No. PCT/EP2018/086631 filed 21 Dec. 2018 and published in English on 4 Jul. 2019 as International Publication No. WO 2019/129719 A1, which claims the benefit of priority under 35 U.S.C. § 119(a) of European Application No. 17211159.3 filed 29 Dec. 2017, each of which are incorporated herein by reference in their entireties.

TECHNICAL FIELD

The present invention relates to an apparatus for extracorporeal blood treatment and a method for controlling the extracorporeal blood treatment apparatus.

In particular, the invention relates to a continuous renal replacement therapy (CRRT) system. CRRT systems are configured for delivering very specific treatments designed for patients versing in acute states of illness and who have temporarily lost their kidney function in its entirety. In this respect, CRRT systems may be structurally and/or operationally different from extracorporeal blood treatment systems designed for chronic patient care.

In contrast to chronic patients, acute patients temporarily experience complete loss of their kidney function typically due to a contemporaneous state of severe injury or during recovery from surgery. Consequently, acute patients are often extremely weak and typically not in a condition to be submitted to regular dialysis treatment, which could further deteriorate their state and lead to serious and possibly life-threatening complications.

Under circumstances as described, CRRT systems are designed to individually treat a patient exhibiting very poor health, without inducing further stress to the patient body, in particular without allowing vital parameters pertaining to the patient's blood to deviate from ideal or near-ideal values.

Within the scope of this document CRRT systems are, thus, inherently characterized by one or more of the following features.

CRRT involves renal replacement therapy, meaning an adjuvant therapy aimed firstly at facilitating continuous fluid removal in diuretic-resistant or acute renal failure patients. Therefore, CRRT systems inherently require a continuous net fluid removal from the patient. In other words, a CRRT system requires a fluid balance control system, such as a weight loss control system, configured to generate a continuous net weight loss rate (as opposed to merely controlling parameters to enable achieving a desired target weight loss as typically found in chronic patient care).

Furthermore, acute patients experience extravascular fluid overload, which cannot be safely removed within a short period of time (e.g. within a few hours of chronic treatment) without causing potentially severe consequences (e.g. hypovolemic shock, arrhythmia, hypoxemia, hypoventilation, etc.). Therefore, a CRRT system must inherently include a much more accurate control over system parameters, in particular flow rates, in order to ensure that the required low flow rates of both blood circulating extra-corporeally and of treatment fluid (infused in the extracorporeal circuit or diffused through the dialyzer) are used.

Moreover, CRRT treatment is performed continuously (e.g. for days or even weeks, without interruption). Therefore, treatment settings in CRRT are based on flow rate settings, rather than settings pertaining to some specified treatment time (which would be unknown as acute patients may require treatment for an unknown time). Consequently, operation of CRRT systems cannot be based on some pre-defined absolute weight loss to be achieved, but rather on a meticulously controlled fluid balance in the patient, requiring continuous adjustments to a number of operating parameters, which have to be controlled and maintained during the entire (and a priori unknown) treatment time, based on a set weight-loss rate.

Additionally, CRRT renal replacement therapy involves therapy substituting kidney functions for a relatively long time period and, thus, a CRRT system further requires at least either fresh dialysis liquid exchange in the dialyzer (in order to remove unwanted substances from blood and to add desired substances to the blood by diffusion) and/or fresh infusion fluid in combination with ultrafiltration (in order to remove unwanted substances from blood and to add desired substances to the blood by convection).

At least for the reasons set forth above, CRRT systems need to exhibit specific technical features enabling the system to:
  Allow setting of a weight loss rate,
  Continuously remove excess water in accordance with a set weight loss rate,
  Operate continuously at comparably low flow rates compatible with CRRT, and
  Balance ion equilibrium by means of proper dialysis being performed and/or by means of substitution fluid continuously being delivered at controlled flow rates.

BACKGROUND OF THE INVENTION

An important issue in CRRT practice is the return of blood contained in the extracorporeal blood circuit, when treatment has to be stopped or interrupted under certain conditions, even though the extracorporeal blood circuit is generally used as long as possible. Conditions under which treatment has to be stopped or interrupted typically include, for example, vascular access problems, clotting occurring in the circuit (e.g. in any component thereof), Delta P and/or transmembrane pressure out of range, (automatically) unmanageable combination of alarms, and similar situations or combinations of the above, but also regular (planned) end of use of a blood circuit. Blood losses are mainly due to the lack of blood return procedures at end of blood circuit use. Non-delivery of blood return procedure may occur due to technical issues and/or caregiver decisions driven by one of more of the following: equivocal clotting diagnostic and users messages which do not well discriminate clotting or membrane plugging events/alarms; lack of user strategy for changing extracorporeal blood circuit before clotting, etc., occurs; organizational issues, for example regarding the time required for starting an unplanned blood return procedure in an emergency situation (e.g. the time may be too long and may often lead to a clotting condition before the effective start of the return procedure, in particular during night shifts involving limited availability of staff). Even though preventive measures, such as citrate anticoagulation, may help to minimize occurrences of the aforementioned conditions, blood losses during CRRT remain significant, if the treatment process has to be stopped immediately, without return of blood from the extracorporeal blood circuit to the patient. WO 2004/069311 describes an extracorporeal blood treatment machine in which a blood circuit is equipped with an inlet line leading to a filtration unit and with an outlet line from the filtration unit. A fluid circuit comprises an inlet line leading to the filtration unit and an outlet line from the filtration unit so as to allow a fluid taken from a primary container to circulate within the filtration unit. There is further an infusion line acting on the outlet line of the blood circuit, which is supplied by an auxiliary fluid container. The inlet line of the fluid circuit is equipped with an infusion branch acting on the outlet line of the blood circuit so as to enable the intensive therapy machine to manage therapies with large exchange of fluids. The described fluid circuit may be used in CRRT.

DE 10011208 describes a filling and/or rinsing method in which a sterile liquid is fed through the extracorporeal blood circulation circuit of the blood dialysis and/or filtration device, with the sterile liquid filtered by passing through the blood dialysis membrane or a sterile filter. A branch line of the extracorporeal blood circulation circuit allows the sterile liquid to be fed to an empty reinfusion container. Also described are a blood dialysis and/or filtration device and a blood hose set for an extracorporeal blood circulation circuit of a blood dialysis and/or filtration device. The described method pertains to hemodialysis only. The reinfusion bag is used only for priming and rinsing and is left full of dialysis fluid so that blood restitution may be performed by opening a clamp and using the liquid contained in the reinfusion bag. After the hemodialysis treatment, the distal end of the blood supply conduit section is disconnected from the cannula, which is connected in the meantime, and is connected to the second outlet of the reinfusion bag. If the branch line branches off from the first section of the blood supply line very close to this distal end, it can also be sufficient to interrupt the cannula connection and simply open the clamp for connection with the reinfusion bag.

EP 2752210 describes a blood purification device similar to that described in document DE 10011208 mentioned above. The blood purification apparatus can suppress air bubbles from flowing to a distal end of an arterial blood circuit during an arterial blood return process and can reduce the burden on health care workers. The blood purification apparatus includes a control device that can perform a venous blood return process in which return of blood is performed by substituting a physiological saline solution for blood from a connection portion connected to a physiological saline solution supplying line to a distal end of a venous blood circuit in a blood circuit during return of blood; an arterial blood return process in which the return of blood is performed by substituting the physiological saline solution for the blood from the connection portion connected to the physiological saline solution supplying line to a distal end of an arterial blood circuit in the blood circuit; and a negative pressure applying process for releasing a negative pressure after applying the negative pressure to a flow route of an upstream side from an arrangement position of a blood pump in the arterial blood circuit, by allowing the blood pump to be in a normal rotation and causing an electromagnetic valve to switch over the physiological saline solution supplying line from a closing state to a circulating state.

None of the above-mentioned documents sufficiently addresses the issues pertaining to CRRT blood restitution described above. Therefore, there is a need for an apparatus and method facilitating an increase in the frequency of successful blood return procedures (e.g. more successfully blood return procedures) during and/or after CRRT. In accordance with embodiments of the present invention, blood contained in the extracorporeal blood circuit is returned to the patient using fluid from sources already connected to the blood treatment apparatus, which fluids are typically used during treatment of a patient (and eventually during priming). In some embodiments, therefore, a portion of fluid contained in any one container connected to the blood treatment apparatus, may be used during regular operation of the apparatus (e.g. during treatment) and a remaining portion of fluid contained in any one of the containers may be used during blood return. In some embodiments, there are several alternative possibilities for blood return, depending upon a remaining amount of fluid present in the container or containers when blood return is to be performed. For the purposes of this description, the term "connected" denotes components that are fluidly connected, or in fluid communication with one another, unless otherwise specified. Thus, for example, a fluid container connected to a fluid line denotes a configuration in which the fluid container is in fluid communication with the fluid line and/or configured to supply fluid to the fluid line. This also pertains to configuration in which the fluid supply and/or the fluid communication is selectively enabled or disabled (e.g. using a valve) and/or otherwise controlled (e.g. using a pump). Fluid flow may be monitored and/or controlled based on signals emitted e.g., by sensors configured to detect a weight of a container and/or a change in weight of a container, or by sensors configured to detect pump speed or pumped volumes. Sensors may include weight sensors (e.g. scales) configured to emit a signal indicative of a weight of a container and/or indicative of a change in weight of a container. Sensors may include sensors for detecting pump revolutions/speed such as Hall sensors and/or sensors for detecting flow rates along infusion tubing. Based on such a signal, for example, a control unit can determine inter alia an amount of fluid present in a container and/or a fluid flow rate from the container. In some embodiments, such fluids include replacement fluid, dialysate fluid, pre-blood-pump (PBP) solution (e.g. for regional anticoagulation), and/or saline solution. Saline solution typically denotes a solution of sodium chloride (NaCl) in water with a concentration of 0.90% w/v of NaCl, 308 mOsm/L or 9.0 g per liter of water. Saline does not generally contain magnesium, calcium and/or potassium ions. The concrete composition of the dialysate may vary depending on the respective treatment. In some examples, dialysate is generally water-based and typically contains controlled amounts of sodium chloride, sodium bicarbonate or sodium acetate, calcium chloride, potassium chloride, and/or magnesium chloride; in some cases optionally glucose or phosphates. In some embodiments, blood return may be activated manually by a user or, for example based on operating parameters of the apparatus, automatically by the control unit of the apparatus.

SUMMARY

A general aim of the present invention is providing an extracorporeal blood treatment apparatus, which generally improves blood return procedures in CRRT, both regular blood return after CRRT has taken place and acute blood return when CRRT is interrupted. In detail it is an aim of the present invention to provide an extracorporeal blood treatment apparatus, which facilitates an increase in the effectiveness of successful blood return procedures in CRRT, and/or which facilitates an increase in the number of successful blood return procedures in CRRT. A further aim of the invention is to make available an extracorporeal blood treatment apparatus provided with an extracorporeal blood circuit, which facilitates an increase in the effectiveness of successful blood return procedures (e.g. more effective blood return procedures) during and/or after CRRT. At least one of the above-indicated aims is attained by an apparatus in accordance with one or more of the appended claims, taken singly or in any combination.

According to a first independent aspect an apparatus for continuous renal replacement therapy is provided, comprising:

a blood circuit (10, 20, 30, 60) comprising a blood removal line (20), a treatment unit (10), and a blood return line (30), the blood treatment unit comprising a semipermeable membrane, a first chamber, and a second chamber, the semipermeable membrane being configured for separating the first chamber from the second chamber, the blood removal line having a first end (20-1) destined to be connected to a vascular system of a subject and a second end (20-2) connected to an inlet port (12) of the first chamber, the blood return line (30) having a first end (30-1) connected to an outlet port (14) of the first chamber and a second end (30-2) destined to be connected to the vascular system;

a replacement fluid container (78) configured for containing a medical fluid;

an infusion line (60; 70; 30) having a first end connected to the replacement fluid container (78) and a second end connected to the blood circuit (10, 20, 30, 60);

a blood pump (22) active on the blood circuit;

a replacement fluid pump (72) active on the pre-infusion line (70);

a control unit (80) connected to the replacement fluid pump (72) and to the blood pump (22) and configured for performing a rinse-back procedure for restituting blood to a patient, particularly at the end of the treatment, the rinse-back procedure comprising:

conveying blood contained in the blood circuit (10, 20, 30, 60) towards the second end (30-2) of the blood return line (30) using the medical fluid, in particular the infusion line may be any of a pre-infusion line (60) connected to the blood removal line (20), a replacement fluid line (70) connected to the blood removal line (20) and a dialysis fluid supply line connected to the blood return line (30).

According to a further independent aspect a rinse-back procedure for restituting blood to a patient in an apparatus for continuous renal replacement therapy is provided, the apparatus comprising a blood circuit (10, 20, 30, 60) comprising a blood removal line (20), a treatment unit (10), and a blood return line (30), the blood treatment unit comprising a semipermeable membrane, a first chamber, and a second chamber, the semipermeable membrane being configured for separating the first chamber from the second chamber, the blood removal line having a first end (20-1) destined to be connected to a vascular system of a subject and a second end (20-2) connected to an inlet port (12) of the first chamber, the blood return line (30) having a first end (30-1) connected to an outlet port (14) of the first chamber and a second end (30-2) destined to be connected to the vascular system; a replacement fluid container (78) configured for containing a medical fluid; a pre-infusion line (70) having a first end (70-1) connected to the replacement fluid container (78) and a second end (70-2) connected to the blood removal line (20); a blood pump (22) active on the blood circuit; a replacement fluid pump (72) active on the pre-infusion line (70); a dialysate circuit (40, 50, 70) comprising an effluent line (50) configured for discharging fluid from the second chamber; a control unit (80) connected to the replacement fluid pump (72) and to the blood pump (22) and configured for performing a rinse-back procedure for restituting blood to a patient, wherein the method includes:

conveying blood contained in the blood circuit (10, 20, 30, 60) towards the second end (30-2) of the blood return line (30) using the medical fluid.

In a $2^{nd}$ aspect according to anyone of the previous aspects, the rinse-back procedure comprises:

preventing fluid flow through the blood removal line (20) proximate the first end (20-1) of the blood removal line before conveying blood contained in the blood circuit (10, 20, 30, 60) towards the second end (30-2) of the blood return line (30) using the medical fluid.

In a $3^{rd}$ aspect according to anyone of the previous aspects, the rinse-back procedure comprises:

conveying blood contained in the blood circuit (10, 20, 30, 60) towards the second end (30-2) of the blood return line using the medical fluid while fluid flow through the blood removal line (20) is being prevented.

In a $4^{th}$ aspect according to anyone of the previous aspects, the second end (70-2) of the pre-infusion line (70) is connected to the blood removal line (20) between the first end (20-1) of the blood removal line (20) and the second end (20-2) of the blood removal line.

In a $5^{th}$ aspect according to anyone of the previous aspects, the apparatus comprises a dialysate circuit (40, 50, 70) having an effluent line (50) configured for discharging fluid from the second chamber.

In a $6^{th}$ aspect according to anyone of the previous aspects, the first end (20-1) of the blood removal line (20) comprises a first connector configured to couple to a vascular access system of a patient.

In a $7^{th}$ aspect according to anyone of the previous aspects, the second end (70-2) of the pre-infusion line (70) is connected to the blood removal line (20) downstream from the first connector proximate the first end (20-1) of the blood removal line and upstream from the second end (20-2) of the blood removal line.

In an $8^{th}$ aspect according to anyone of the previous aspects, the second end (70-2) of the pre-infusion line (70) is connected to the blood removal line (20) at a pre-infusion site (20-3b) located downstream from the blood pump (22) and upstream from the second end (20-2) of the blood removal line.

In a $9^{th}$ aspect according to anyone of the previous aspects, the blood circuit (10, 20, 30, 60) includes a blood pump tract (22t), the blood pump (22) being active on the blood pump tract.

In a $10^{th}$ aspect according to anyone of the previous aspects, the blood removal line (20) comprises the blood pump tract (22t).

In an $11^{th}$ aspect according to anyone of the previous aspects, the apparatus further comprises:

a second pre-infusion line (60);

a PBP fluid pump (62) connected to the control unit (80) and active on the second pre-infusion line (60); and a PBP fluid container (68) configured for containing a second medical fluid; wherein the second pre-infusion line (60) has a first end (60-1) connected to the PBP fluid container (68) and a second end (60-2) connected to the blood removal line (20).

In a $12^{th}$ aspect according to the preceding aspect, the second end (60-2) of the second pre-infusion line (60) is connected to the blood removal line (20) downstream from the first end (20-1) of the blood removal line and upstream from the second end (20-2) of the blood removal line.

In a $13^{th}$ aspect according to any one of the two preceding aspects, the second end (60-2) of the second pre-infusion line (60) is connected to the blood removal line (20) downstream from the first end (20-1) of the blood removal line and upstream from the blood pump (22).

In a $14^{th}$ aspect according to any one of aspects 11 to 13, the second medical fluid is different from the medical fluid.

In a 15th aspect according to any one of aspects 11 to 14, the second medical fluid includes a solution configured for regional anticoagulation.

In a 16th aspect according to any one of aspects 11 to 15, the second medical fluid includes citrate and/or citric acid, or a mix of both.

In a 17th aspect according to any one of aspects 11 to 16, the second pre-infusion line (60) comprises a PBP fluid pump tract (62t), the PBP fluid pump (62) being active on the PBP fluid pump tract (62t).

In an 18th aspect according to anyone of the previous aspects, the apparatus further comprises an air separator (35) arranged on the blood return line (30), and optionally a sensor for determining fluid level in the air separator.

In a 19th aspect according to anyone of the previous aspects, the apparatus further comprises an air bubble detector arranged on the blood return line (30), particularly placed downstream the air separator (35).

In a 20th aspect according to anyone of the previous aspects, the apparatus further comprises a blood warmer (33) arranged on the blood return line (30).

In a 21st aspect according to the preceding aspect and to aspect 18, the blood warmer (33) is positioned on the blood return line (30) upstream from the air separator (35) based on a direction of fluid flow through the blood return line (30) from the first end (30-1) towards the second end (30-2) of the blood return line (30).

In a 22nd aspect according to anyone of the previous aspects, the apparatus further comprises a gas exchanger arranged in the blood circuit (10, 20, 30, 60).

In a 23rd aspect according to anyone of the previous aspects, the apparatus further comprises a PBP fluid sensor (69) connected to the control unit (80) and configured to generate a PBP fluid signal indicative of an amount of PBP fluid present in the PBP fluid container (68).

In a 24th aspect according to anyone of the previous aspects, the control unit (80) is further configured to, or the procedure includes, determine, based on the PBP fluid signal, a PBP amount signal indicative of an amount of PBP fluid present in the PBP fluid container (68).

In a 25th aspect according to any one of the two preceding aspects, the control unit (80) is further configured to, or the procedure includes, determine, based on changes of the PBP fluid signal over time, a PBP flow rate signal indicative of a flow rate of PBP fluid flowing from the PBP fluid container (68).

In a 26th aspect according to anyone of the previous aspects, the apparatus further comprises a PBP sensor connected to the control unit (80) and configured to generate a PBP signal indicative of a substantially empty container, said PBP sensor being for example an air sensor placed on the second pre-infusion line (60).

In a 27th aspect according to anyone of the previous aspects, the pre-infusion line (70) comprises a pre-infusion pump tract (72t), the replacement fluid pump (72) being active on the pre-infusion pump tract.

In a 28th aspect according to anyone of the previous aspects, the rinse-back procedure comprises:
conveying blood contained in the blood circuit (10, 20, 30, 60) towards the second end (30-2) of the blood return line using the medical fluid of the replacement fluid container (78) and/or a second medical fluid of a PBP fluid container (68), while fluid flow through the blood removal line (20) is being prevented.

In a 29th aspect according to anyone of the previous aspects, the apparatus further comprises:
a post-infusion line (70b); and
a pre/post-infusion branch (73); wherein
the pre/post-infusion branch (73) is arranged on the pre-infusion line (70) downstream from the replacement fluid pump (72) based on a direction of fluid flow from the first end (70-1) towards the second end (70-2) of the replacement fluid line;
the post-infusion line (70b) has a first end (70b-1) connected to the pre/post-infusion branch (73); and
the pre/post-infusion branch (73) is configured to selectively enable fluid flow:
between the first end (70-1) and the second end (70-2) of the pre-infusion line (70); or
between the first end (70-1) of the pre-infusion line (70) and the second end (70b-2) of the post-infusion line (70b).

In a 30th aspect according to the preceding aspect, the second end (70b-2) of the post-infusion line (70) is connected to the blood return line (30) between the first end (30-1) of the blood return line (30) and the second end (30-2) of the blood return line (30).

In a 31st aspect according to the preceding aspect in combination with aspect 18, the second end (70b-2) of the post-infusion line (70) is connected to the air separator (35) and configured to enable introduction of fluid supplied through the post-infusion line (70b) into the sir separator (35).

In a 32nd aspect according to anyone of the previous aspects, the apparatus further comprises:
a dialysate container (48) configured for containing dialysate;
a dialysate line (40) having a first end (40-1) connected to the dialysate container and a second end (40-2) connected to an inlet port (16) of the second chamber; and
a dialysate pump (42) connected to the control unit (80) and active on the dialysate line.

In a 33rd aspect according to the preceding aspect, the dialysate line (40) comprises a dialysate pump tract (42t), the dialysate pump (42) being active on the dialysate pump tract.

In a 34th aspect according to anyone of the previous aspects, the apparatus further comprises an effluent pump (52) connected to the control unit (80) and active on the effluent line (50), wherein the effluent line (50) has a first end (50-1) connected to the outlet port (18) of the second chamber and a second end (50-2) configured for discharging fluid.

In a 35th aspect according to the preceding aspect, the effluent line (50) comprises an effluent pump tract (52t), the effluent pump (52) being active on the effluent pump tract In a 36th aspect according to any one of the two preceding aspects, the apparatus further comprises an effluent fluid container (58) configured for receiving fluid, wherein the second end (50-2) of the effluent line (50) is connected to the effluent fluid container (58) and configured for discharging fluid into the effluent fluid container (58).

In a 37th aspect according to any one of aspects 30 or 31, the second end (50-2) of the effluent line (50) is connected to a drain configured for receiving fluid, the second end (50-2) of the effluent line (50) being configured for discharging fluid into the drain.

In a 38th aspect according to any one of the two preceding aspects, the apparatus further comprises:
a second dialysate line (40b); and
a dialysate branch (43); wherein
the dialysate branch (43) is arranged on the dialysate line (40) downstream from the dialysate pump (42) based on a direction of fluid flow from the first end (40-1) to the second end (40-2) of the dialysate line;
the second dialysate line (40b) has a first end (40b-1) connected to the dialysate branch (43) and a second end (40b-2) connected to the post-infusion line (70b); and
the dialysate branch (43) is configured to selectively enable fluid flow:
between the first end (40-1) and the second end (40-2) of the dialysate line (40); or
between the first end (40-1) of the dialysate line (40) and the second end (40b-2) of the second dialysate line (40b).

In a 39th aspect according to the preceding aspect, the second end (40b-2) of the second dialysate line (40b) is connected to the post-infusion line (70b) downstream from the pre/post-infusion branch (73) with respect to a direction of fluid flow from the pre/post-infusion branch (73) towards the second end (70b-2) of the post-infusion line (70b).

In a 40th aspect according to anyone of the previous aspects, the control unit (80) is further configured to, or the procedure includes, determine a selected rinse-back mode from a group comprising one or more of a first rinse-back mode, a second rinse-back mode, a third rinse-back mode, a fourth rinse-back mode, and a fifth rinse-back mode.

In a 41st aspect according to the preceding aspect, the control unit (80) is further configured to, or the procedure includes, determine the selected rinse-back mode at least based on an amount of the medical fluid present in at least the fluid container.

In a 42nd aspect according to anyone of the previous aspects, the apparatus further comprises a replacement fluid sensor (79) connected to the control unit (80) and configured to generate a replacement fluid signal indicative of an amount of replacement fluid present in the replacement fluid container (78).

In a 43rd aspect according to the preceding aspect, the control unit (80) is further configured to, or the procedure includes, determine, based on the replacement fluid signal, a replacement fluid amount signal indicative of an amount of replacement fluid present in the replacement fluid container (78).

In a 44th aspect according to any one of the two preceding aspects, the control unit (80) is further configured to, or the procedure includes, determine, based on changes of the replacement fluid signal over time, a replacement fluid flow rate signal indicative of a flow rate of replacement fluid flowing from the replacement fluid container (78).

In a 45th aspect according to anyone of the previous aspects, the apparatus further comprises a replacement sensor connected to the control unit (80) and configured to generate a replacement signal indicative of a substantially empty container, said replacement sensor being for example an air sensor placed on the pre-infusion line (70).

In a 46th aspect according to any one of the two preceding aspects, the apparatus further comprises a dialysate sensor (49) connected to the control unit (80) and configured to generate a dialysate signal indicative of an amount of dialysate present in the dialysate container (48).

In a 47th aspect according to the preceding aspect, the control unit (80) is further configured to, or the procedure includes, determine, based on the dialysate signal, a dialysate amount signal indicative of an amount of dialysate present in the dialysate container (48).

In a 48th aspect according to any one of the two preceding aspects, the control unit (80) is further configured to, or the procedure includes, determine, based on changes of the dialysate signal over time, a dialysate flow rate signal indicative of a flow rate of dialysate flowing from the dialysate container (48).

In a 49th aspect according to anyone of the previous aspects, the apparatus further comprises a dialysate sensor connected to the control unit (80) and configured to generate a dialysate signal indicative of a substantially empty container, said dialysate sensor being for example an air sensor placed on the dialysate line (40).

In a 50th aspect according to anyone of the previous aspects, the apparatus further comprises an effluent fluid sensor (59) connected to the control unit (80) and configured to generate an effluent fluid signal indicative of an amount of effluent fluid present in the effluent fluid container (58).

In a 51st aspect according to the preceding aspect, the control unit (80) is further configured to, or the procedure includes, determine, based on the effluent fluid signal, an effluent fluid amount signal indicative of an amount of effluent fluid present in the effluent fluid container (58).

In a 52nd aspect according to any one of the two preceding aspects, the control unit (80) is further configured to determine, based on changes of the effluent fluid signal over time, an effluent fluid flow rate signal indicative of a flow rate of effluent fluid flowing into the effluent fluid container (58).

In a 53rd aspect according to any one of the two preceding aspects, the control unit (80) is further configured for, or the procedure includes, collecting replacement pump operational data indicative of an operation history of the replacement fluid pump (72) and for determining a residual fluid amount present in the replacement fluid container (78) based on the replacement pump operational data.

In a 54th aspect according to the preceding aspect, the replacement fluid pump (72) includes an occlusive pump, e.g. a peristaltic pump, and the replacement pump operational data include one or more of a plurality of flow rates performed by the replacement fluid pump (72) over time and a number of revolutions performed by the replacement fluid pump (72) over time.

In a 55th aspect according to anyone of the previous aspects in combination with aspect 11, the control unit (80) is further configured for, or the procedure includes, collecting PBP pump operational data indicative of an operation history of the PBP fluid pump (62) and for determining a residual fluid amount present in the PBP fluid container (68) based on the PBP pump operational data.

In a 56th aspect according to the preceding aspect, the PBP fluid pump (62) includes an occlusive pump, e.g. a peristaltic pump, and the PBP pump operational data include one or more of a plurality of flow rates performed by the PBP fluid pump (72) over time and a number of revolutions performed by the PBP fluid pump (72) over time.

In a 57th aspect according to anyone of the previous aspects, the control unit (80) is further configured for, or the procedure includes, monitoring an amount of fluid present in the replacement fluid container (78) at the time of activation of the rinse-back procedure.

In a 58th aspect according to anyone of the previous aspects in combination with aspect 11, the control unit (80) is further configured for, or the procedure includes, monitoring an amount of fluid present in the PBP fluid container (68) at the time of activation of the rinse-back procedure.

In a 59th aspect according to anyone of the previous aspects, the blood pump (22) includes an occlusive pump, e.g. a peristaltic pump.

In a 60th aspect according to anyone of the previous aspects in combination with aspect 32, wherein the control unit (80) is further configured for, or the procedure includes, collecting dialysate pump operational data indicative of an operation history of the dialysate pump (42) and for determining a residual fluid amount present in the dialysate container (48) based on the dialysate pump operational data.

In a 61st aspect according to the preceding aspect, the dialysate pump (42) includes an occlusive pump, e.g. a peristaltic pump, and the dialysate pump operational data include one or more of a plurality of flow rates performed by the dialysate pump (52) over time and a number of revolutions performed by the dialysate pump (52) over time.

In a 62nd aspect according to anyone of the previous aspects, the medical fluid includes dialysis liquid with sodium and chloride ions, optionally wherein the dialysis liquid includes one or more of calcium ions, potassium ions and magnesium ions.

In a 63rd aspect according to the preceding aspect, the dialysis liquid is different in composition from saline solution.

In a 64th aspect according to anyone of the previous aspects, the second end (30-2) of the blood return line (30) comprises a second connector configured to couple to a vascular access system of a patient.

In a 65th aspect according to the preceding aspect, during the rinse-back procedure, the second connector is connected to the vascular access system of a patient.

In a 66th aspect according to anyone of the previous aspects in combination with aspect 6, during the rinse-back procedure, the first connector is connected to the vascular access system of a patient.

In a 67th aspect according to anyone of the previous aspects in combination with aspect 40, wherein the control unit (80) is further configured to, or the procedure includes, determine the selected rinse-back mode based on an amount of the medical fluid present in the replacement fluid container (78) and an amount of the second medical fluid present in the PBP fluid container.

In a 68th aspect according to anyone of the previous aspects in combination with aspects 40 and 11, the control unit (80) is configured for performing the rinse-back procedure according to the first mode (100) and wherein the rinse-back procedure further comprises:
  blocking a fluid flow towards a first end (20-1) of the blood removal line (20);
  enabling (108) fluid flow through the blood return line (30);
  controlling (110) the blood pump (22) and the PBP pump (62) to convey fluid from the PBP fluid container (68) towards the treatment unit (10);
  controlling (112) the blood pump (22) and the PBP pump (62) to stop conveying fluid when a second predetermined amount of fluid has been conveyed;
  controlling (114) the replacement fluid pump (72) to convey fluid from the replacement fluid container (78) towards the treatment unit (10);
  controlling (116) the replacement fluid pump (72) to stop conveying fluid when an eighth predetermined amount of fluid has been conveyed; and, optionally
  disabling (118) fluid flow through the blood return line (30).

In a 69th aspect according to the preceding aspect, the control unit (80) is configured for, or the procedure includes, enabling the rinse-back procedure according to the first mode, if an amount of fluid present in the replacement fluid container (78) is equal to or greater than the eighth predetermined amount and an amount of fluid present in the PBP fluid container (68) is equal to the second predetermined amount, the second predetermined amount being for example $\alpha \cdot V2$,
wherein
$\alpha$ is a constant value, and
V2 is a volume of the blood circuit included between a first and a second pre infusion sites (20-3b, 20-3a).

In a 70th aspect according to anyone of the previous aspects, the control unit (80) is configured for performing the rinse-back procedure according to the second mode (200) and wherein the rinse-back procedure further comprises:
  blocking a fluid flow towards a first end (20-1) of the blood removal line (20);
  enabling (208-108) fluid flow through the blood return line (30);
  controlling (208-110) the blood pump (22) and the PBP pump (62) to convey fluid from the PBP fluid container (68) towards the treatment unit (10);
  controlling (208-112) the blood pump (22) and the PBP pump (62) to stop conveying fluid when a second predetermined amount of fluid has been conveyed;
  controlling (208-114) the replacement fluid pump (72) to convey fluid from the replacement fluid container (78) towards the treatment unit (10); and
  if the amount of fluid conveyed by the replacement fluid pump (72) is less than the eighth predetermined amount of fluid, controlling (214) the blood pump (22) and the PBP pump (62) to convey fluid from the PBP fluid container (68) towards the treatment unit (10) until a total amount of fluid conveyed reaches the eighth predetermined amount of fluid; and, optionally
  disabling (218) fluid flow through the blood return line (30).

In a 71st aspect according to anyone of the previous aspects, the control unit (80) is configured for performing the rinse-back procedure according to the third mode (300) and wherein the rinse-back procedure further comprises:
  enabling (308) fluid flow through the blood return line (30);
  controlling (310) the blood pump (22) and the PBP pump (62) to convey fluid from the PBP fluid container (68) towards the treatment unit (10);
  controlling (312) the blood pump (22) and the PBP pump (62) to stop conveying fluid when a ninth predetermined amount of fluid has been conveyed; and, optionally
  disabling (314) fluid flow through the blood return line (30).

In a 72nd aspect according to anyone of the previous aspects in combination with aspect 40, wherein the control unit (80) is configured for performing the rinse-back procedure according to the fourth mode (400) and wherein the rinse-back procedure further comprises:
  controlling (404) the blood pump (22) to convey blood towards the treatment unit (10);
  controlling (406) the blood pump (22) to stop conveying blood when a tenth predetermined amount of blood has been conveyed;
  controlling (408) the replacement fluid pump (72) to convey fluid at a first flow rate from the replacement fluid container (78) towards the treatment unit (10) and, after a predetermined pumped fluid volume, controlling (410) the blood pump (22) to convey fluid in reverse at a second flow rate towards the first end (20-1) of the blood removal line (20), the first flow rate being higher than the second flow rate, optionally the first flow rate being about two times the second flow rate;

controlling (412) the replacement fluid pump (72) to stop conveying fluid when a first target amount of fluid has been conveyed and controlling (414) the blood pump (22) to stop conveying fluid when a second target amount of fluid has been conveyed; and, optionally disabling (416) fluid flow through the blood return line (30).

In a 73$^{rd}$ aspect according to anyone of the previous aspects in combination with aspect 40, wherein the control unit (80) is configured for performing the rinse-back procedure according to the fifth mode (500) and wherein the rinse-back procedure further comprises:

enabling (504) fluid flow through the blood return line (30);

controlling (506) the replacement fluid pump (72) to convey fluid from the replacement fluid container (78) towards the treatment unit (10);

controlling (508) the replacement fluid pump (72) to stop conveying fluid when an eighth predetermined amount of fluid has been conveyed; and, optionally disabling (510) fluid flow through the blood return line (30).

In a 74$^{th}$ aspect according to anyone of the previous aspects 70, 71, or 73, wherein the control unit (80) is configured for, or the procedure includes, enabling the rinse-back procedure according to one of the second mode (200), the third mode (300), and the fifth mode (500), if an amount of fluid present in the replacement fluid container (78) is equal to or greater than an eighth pre-determined amount and an amount of fluid present in the PBP fluid container (68) is equal to a second predetermined amount; and the control unit is configured for disabling the rinse-back procedure according to the second mode, the third mode, and the fifth mode, if the amount of medical fluid present in the fluid container is less than the pre-determined minimum amount.

In a 75$^{th}$ aspect according to anyone of the previous aspects 68, 70, 71, or 73, wherein the rinse-back procedure further comprises, prior to the step of enabling fluid flow through the blood return line (30):

prompting a user to disable fluid flow through the blood removal line (30); and checking whether fluid flow through the blood removal line (30) has been disabled.

In a 76$^{th}$ aspect according to anyone of the previous aspects 68, 70, 71, 72 and 73, wherein the rinse-back procedure (100, 200, 300, 400, 500) further comprises performing (102, 202, 302, 402, 502) a status check; optionally wherein performing the status check includes determining an amount of fluid in one or more of the PBP fluid container (68), the dialysate container (48), and the replacement fluid container (78).

In a 77$^{th}$ aspect according to anyone of the previous aspects, the apparatus further comprises a first flow controller (27) connected to the control unit (80) and active on the blood removal line (20) and/or a second flow controller (37) connected to the control unit (80) and active on the blood return line (30).

In a 78$^{th}$ aspect according to the preceding aspect, the first (27) and second (37) flow controllers each include a corresponding clamp mechanism operably coupled respectively to the blood removal line (20) and to the blood return line (30).

In a 79$^{th}$ aspect according to anyone of the previous three aspects, the control unit (80) is configured for, or the procedure includes, controlling the first (27) and second (37) flow controllers to selectively disable fluid flow respectively through the blood removal line (20) and/or the blood return line (30).

In an 80$^{th}$ aspect according to anyone of the previous aspects, the apparatus further comprises:

a second pre-infusion line (60);

a PBP fluid pump (62) connected to the control unit (80) and active on the second pre-infusion line (60); and a PBP fluid container (68) configured for containing a citrate solution; the second pre-infusion line (60) having a first end (60-1) connected to the PBP fluid container (68) and a second end (60-2) connected to the blood removal line (20), wherein the control unit (80) stores PBP flow rate during treatment, during the rinse-back procedure, the control unit (80) is configured to infuse less than the equivalent of 10 min of mean PBP flow rate.

In an 81$^{st}$ aspect according to anyone of the previous aspects, the rinse-back procedure comprises:

a) blocking a fluid flow towards a first end (20-1) of the blood removal line (20);

b) enabling (108; 308) fluid flow through the blood return line (30);

e) controlling (114; 408) the replacement fluid pump (72) to convey fluid at a first flow rate from the replacement fluid container (78) towards the treatment unit (10);

f) controlling (116; 412) the replacement fluid pump (72) to stop conveying fluid when a second predetermined amount of fluid has been conveyed; and, optionally h) disabling (118; 218; 314; 416) fluid flow through the blood return line (30).

In an 82$^{nd}$ aspect according to anyone of the previous aspects, the apparatus further comprises:

a second pre-infusion line (60);

a PBP fluid pump (62) connected to the control unit (80) and active on the second pre-infusion line (60); and a PBP fluid container (68) configured for containing a second medical fluid, in particular the second medical fluid including a solution for regional anticoagulation; wherein the second pre-infusion line (60) has a first end (60-1) connected to the PBP fluid container (68) and a second end (60-2) connected to the blood removal line (20), the second end (60-2) of the second pre-infusion line (60) being connected to the blood removal line (20) downstream from the first end (20-1) of the blood removal line and upstream from the blood pump (22);

wherein the rinse-back procedure further comprises:

c) controlling (110; 310) the blood pump (22) and the PBP pump (62) to convey fluid from the PBP fluid container (68) towards the treatment unit (10);

d) controlling (112; 312) the blood pump (22) and the PBP pump (62) to stop conveying fluid when a first predetermined amount of fluid has been conveyed.

In an 83$^{rd}$ aspect according to the previous aspect, the apparatus further comprises a PBP fluid sensor (69) connected to the control unit (80) and configured to generate a PBP fluid signal indicative of an amount of PBP fluid present in the PBP fluid container (68), in particular wherein the control unit (80) is further configured to determine, based on changes of the PBP fluid signal over time, a PBP flow rate signal indicative of a flow rate of PBP fluid flowing from the PBP fluid container (68).

In an 84th aspect according to the previous aspect, at the time of activation of the rinse-back procedure, the control unit (80) is configured to check whether the amount of PBP fluid is higher than the first predetermined amount of fluid and, in case amount of PBP fluid is less than the first predetermined amount of fluid, to:
  issue a warning; and/or
  controlling (112; 312) the blood pump (22) and the PBP pump (62) to stop conveying fluid when the amount of PBP fluid has been conveyed.

In an 85th aspect according to anyone of the previous three aspects, the rinse-back procedure comprises:
  conveying blood contained in the blood circuit (10, 20, 30, 60) towards the second end (30-2) of the blood return line using the medical fluid of the replacement fluid container (78) and/or a second medical fluid of a PBP fluid container (68), while fluid flow through the blood removal line (20) is being prevented.

In an 86th aspect according to anyone of the previous four aspects, when depending on aspect 81, steps c) and d) are performed before steps e) and f).

In an 87th aspect according to anyone of the previous four aspects, when depending on aspect 81, the rinse-back procedure further comprises:
g) controlling (214) the blood pump (22) and the PBP pump (62) to convey fluid from the PBP fluid container (68) towards the treatment unit (10) until a total amount of fluid conveyed reaches a third predetermined amount of fluid, wherein step g) is performed after steps e) and f).

In an 88th aspect according to the previous aspects 87 and 82, the control unit (80) is configured to check whether the amount of PBP fluid is higher than the sum of the first and third predetermined amount of fluid and, in case amount of PBP fluid is less than the sum, to:
  issue a warning; and/or
  controlling (112; 312) the blood pump (22) and the PBP pump (62) to stop conveying fluid when the amount of PBP fluid has been conveyed.

In an 89th aspect according to anyone of the previous aspects 81 to 88, the rinse-back procedure further comprises:
e') during step e) and after a predetermined pumped fluid volume with the replacement fluid pump (72), controlling (410) the blood pump (22) to convey fluid in reverse at a second flow rate towards the first end (20-1) of the blood removal line (20), the first flow rate being higher than the second flow rate, optionally the first flow rate being about two times the second flow rate;
f') controlling (414) the blood pump (22) to stop conveying fluid when a target amount of fluid has been conveyed.

In a 90th aspect according to the previous aspect, the rinse-back procedure further comprises:
I) enabling fluid flow through the blood removal line (20);
II) enabling fluid flow through the blood return line (30);
III) after steps I) and II), controlling (404) the blood pump (22) to convey blood towards the treatment unit (10);
IV) controlling (406) the blood pump (22) to stop conveying blood when a fourth predetermined amount of blood has been conveyed;
wherein steps I) to IV) are performed before step a).

In a 91st aspect according to anyone of the previous aspects 81 to 90, the rinse-back procedure further comprises, prior to the step b):
  prompting a user to disable fluid flow through the blood removal line (30); and
  checking whether fluid flow through the blood removal line (30) has been disabled.

In a 92nd aspect according to the previous aspects 43 and 81, at the time of activation of the rinse-back procedure, the control unit (80) is configured to check whether the amount of replacement fluid present in the replacement fluid container (78) is higher than the second predetermined amount of fluid and, in case amount of replacement fluid is less than the second predetermined amount of fluid, to:
  issue a warning; and/or
  controlling (116; 412) the replacement fluid pump (72) to stop conveying fluid when the amount of replacement fluid has been conveyed.

In a 93rd aspect according to anyone of the previous aspects, the control unit (80) is configured for performing a patient extracorporeal blood treatment procedure before the rinse-back procedure, the patient extracorporeal blood treatment procedure comprising:
  withdrawing blood from the patient through the blood removal line (20);
  treating blood in the treatment unit (10);
  returning blood to the patient through the blood return line (30);
  injecting the medical fluid from the replacement fluid container (78) into the blood circuit (10, 20, 30, 60).

In a 94th aspect according to anyone of the previous aspects, the control unit (80) is configured for performing a patient extracorporeal blood treatment procedure before the rinse-back procedure, the patient extracorporeal blood treatment procedure comprising:
  injecting the medical fluid from the replacement fluid container (78) into the blood circuit (10, 20, 30, 60).

In a 95th aspect according to anyone of the previous aspects, the control unit (80) is configured for performing a patient extracorporeal blood treatment procedure before the rinse-back procedure, the patient extracorporeal blood treatment procedure comprising:
  injecting the second medical fluid from the PBP fluid container (68) into the blood circuit (10, 20, 30, 60), particularly in the blood removal line (20).

In a 96th aspect according to anyone of the previous aspects, the control unit (80) is configured for performing a patient extracorporeal blood treatment procedure before the rinse-back procedure, the patient extracorporeal blood treatment procedure comprising:
  enabling a blood flow from a first end (20-1) of the blood removal line (20);
  enabling (108; 308) a blood flow through the blood return line (30).

In a 97th aspect according to anyone of the previous aspects, the replacement fluid container (78) is a flexible bag, e.g. a 5 L liquid bag.

In a 98th aspect according to the previous aspect 11, the PBP fluid container (68) is a flexible bag.

In a 99th aspect according to the previous aspect 32, the dialysate container (48) is a flexible bag.

Further characteristics and advantages of the present invention will better emerge from the detailed description that follows of at least an embodiment of the invention, illustrated by way of non-limiting example in the accompanying figures of the drawings.

BRIEF DESCRIPTION OF THE DRAWINGS

The description will now follow, with reference to the appended figures, provided by way of non-limiting example, in which:

FIG. 3A shows a flow chart of a process for rinsing back blood from an extracorporeal blood circuit to a patient in accordance with a first embodiment of the present invention;

FIG. 4 shows a flow chart of a process for rinsing back blood from an extracorporeal blood circuit to a patient in accordance with a third embodiment of the present invention;

DETAILED DESCRIPTION

Figure 1:
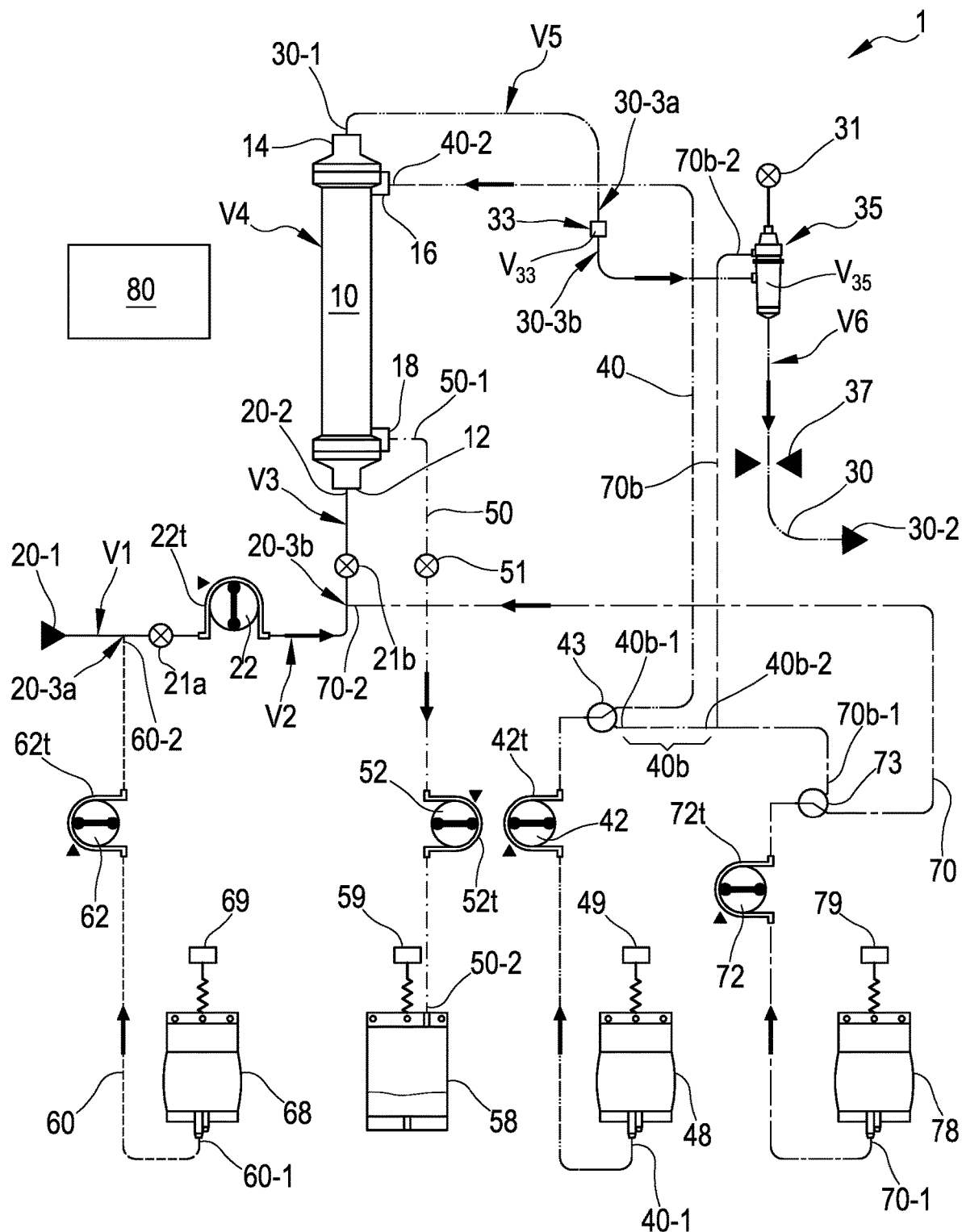
FIG. 1 schematically shows the extracorporeal blood circuit of an extracorporeal blood treatment apparatus in accordance with embodiments of the present invention.

FIG. 1 schematically shows the extracorporeal blood circuit of an extracorporeal blood treatment apparatus in accordance with embodiments of the present invention.

An example of an extracorporeal blood circuit is schematically illustrated, but it is noted that the specific structure of the hydraulic circuit is not relevant for the purposes of the present invention and therefore other and different circuits to those specifically shown in FIG. 1 might be used in consequence of the functional and design needs of each single medical apparatus. Generally, the hydraulic circuit includes at least a blood circuit 10, 20, 30 (and, optionally, 33, 35) and a dialysate circuit 10, 40, 50. It is noted that the first chamber of treatment unit 10 is understood to be part of the blood circuit 10, 20, 30, and that the second chamber of treatment unit 10 is understood to be part of the dialysate circuit 10, 40, 50. Thus, treatment unit 10 may be considered a component of both the blood circuit and the dialysate circuit. In some embodiments, the hydraulic circuit includes additional fluid lines 40b, 60, 70, 70b. The hydraulic circuit exhibits a blood circuit including a blood removal line 20, a treatment unit 10, and a blood return line 30. The blood removal line 20 has a first end 20-1 designed to connect to the vascular system of a patient. In some embodiments, the first end 20-1 of the blood removal line 20 includes a connector (e.g. a Luer connector) configured to connect to a vascular access system of a patient. The particular manner of fluidly connecting the first end 20-1 of the blood removal line 20 to the vascular system of a patient may be realized in accordance with known components and methods. The blood removal line 20 further includes a second end 20-2 configured to connect to the treatment unit 10, in particular to an inlet port 12 of a first chamber of the treatment unit 10. The blood return line 30 has a first end 30-1 configured to connect to the treatment unit 10, in particular to an outlet port 14 of the first chamber of the treatment unit 10. The blood return line 30 further has a second end 30-2 designed to connect to the vascular system of the patient. In some embodiments, the second end 30-2 of the blood return line 30 includes a connector (e.g. a Luer connector) configured to connect to a vascular access system of a patient. The particular manner of fluidly connecting the second end 30-2 of the blood return line 30 to the vascular system of a patient may be realized in accordance with known components and methods. The treatment unit 10, for example a dialyzer, a plasma filter, a hemofilter, a hemodiafilter or an adsorpition device, generally includes a first chamber and a second chamber, which are separated by a semipermeable membrane, for example of the hollow-fiber type or of the plate type. The treatment unit 10 includes the inlet port 12 and the outlet port 14, respectively configured to put the first chamber in fluid communication with the second end 20-2 of the blood removal line 20 and with the first end 30-1 of the blood return line 30. The hydraulic circuit further includes a dialysis line 40 configured for supplying dialysate to the treatment unit 10 and an effluent line 50 configured for discharging used fluid from the treatment unit 10 towards a drain or into a corresponding effluent fluid container. The dialysate line 40 has a first end 40-1 configured to connect to a dialysate container 48, such as a dialysate bag or other source of dialysate fluid, and a second end 40-2 configured to connect to an inlet port 16 of the second chamber of the treatment unit 10. The effluent line 50 has a first end 50-1 configured to connect to an outlet port 18 of the second chamber of the treatment unit 10 and a second end 50-2 configured to connect to an effluent fluid container 58 configured to receive used fluid from the second chamber of the treatment unit 10. In some embodiments, the second end 50-2 of the effluent line may be directly connected to a drain and configured to discharge used fluid directly to the drain. The treatment unit 10 further includes the inlet port 16 and the outlet port 18, respectively configured to put the second chamber in fluid communication with the second end 40-2 of the dialysate line 40 and with the first end 50-1 of the effluent line. The hydraulic circuit may also comprise one or more air separators 35 and/or blood warmers 33 and or gas exchangers. In the example of FIG. 1, the blood return line 30 includes an air separator 35. Further, the blood return line 30 includes a blood warmer 33 arranged upstream from the air separator 35 and configured to control a temperature of fluid flowing through the blood return line 30. Other air separators may be present in the blood circuit, for example positioned on the blood removal line 20. In case a gas exchanger for $CO_2$ removal is present in the circuit, the gas exchanger can be placed either upstream or downstream the treatment unit 10. Within the scope of this description, the terms "upstream" and "downstream" are based on a general direction of fluid flow along a fluid line and/or through components of the apparatus under treatment condition (e.g. generally from a first end of a line towards a second end of a line; and/or from an arterial access of a patient towards a venous access of a patient). In general (e.g. during treatment), fluid flows through the blood removal line 20, treatment unit 10, and blood return line 30 from the first end 20-1 of the blood removal line 20 towards the second end 30-2 of the blood return line 30. Further, fluid generally flows from containers 48, 68, and 78 towards the blood circuit, while used fluid flows from the treatment unit 10 towards and into container 58 (or, alternatively, towards and into a drain; not shown). Unless otherwise specified, the terms upstream and downstream refer to the above general directions of fluid flow through lines and components during regular operation of the apparatus (e.g. during treatment). The hydraulic circuit further includes a replacement fluid container 78 and a pre-infusion line 70 having a first end 70-1 configured to connect to the replacement fluid container 78 and a second end 70-2 configured to connect to the blood removal line 20. The hydraulic circuit further includes a blood pump 22 and a replacement fluid pump 72. The extracorporeal blood treatment apparatus 1 further comprises a control unit 80, i.e. a programmed/programmable control unit, configured to control components of the hydraulic circuit (e.g. pumps, valves, clamps) and to receive signals from components (e.g. sensors). FIG. 1 merely schematically shows control unit 80 as a separate component, because for reasons of clarity the individual connections between control unit 80 and other components of the extracorporeal blood treatment apparatus 1 are not shown. It is understood, however, that control unit 80 is connected to, for example, pumps (e.g. blood pump 22 and replacement fluid pump 78, as well as any other pumps, if present), sensors (e.g. sensors 21a, 21b, 31, 49, 59, 69, 79). This list of components controlled by or configured to send signals to the control unit 80 is not exhaustive. Other components may be connected to control unit 80 as generally known in the field.

The control unit 80 may, for example, comprise one or more digital microprocessor units or one or more analog units or other combinations of analog units and digital units. Relating, by way of example, to a microprocessor unit, once the unit has executed a specific program (for example a remotely supplied program or a locally stored program directly integrated into the microprocessor card or an associated memory unit), the unit is programmed, defining a plurality of functional blocks which constitute means each designed to perform respective operations as described in detail below. In some embodiments, the extracorporeal blood treatment apparatus 1 may further comprise a user interface (e.g. a graphic user interface or GUI). For reasons of clarity, the user interface is not shown in FIG. 1. The user interface is also connected to control unit 80 and configured to both present information to a user or operator by means of an output unit (e.g. screen, touchscreen, monitor, led elements, etc.) and to receive input from the user/operator by means of an input unit (e.g. keyboard, hardware button(s), mouse, touchscreen, voice recognition, optical recognition). The extracorporeal blood treatment apparatus 1 may further comprise one or more sensors configured to detect presence or absence of disposable or replaceable components and a corresponding type thereof. Such one or more sensors may include optical sensors, for example barcode or QR-code readers configured to read barcodes/QR-codes associated with components such as blood sets/circuits or cartridges. Such one or more sensors may further include radiofrequency or other sensors, for example RFID readers configured to read data from active/passive RFID-Tags associated with components such as fluid containers, blood sets/circuits, or cartridges. It is understood that the control unit 80 may collect configuration data, operational data, and/or status data from one or more components before, during, and after operation of the apparatus and/or treatment. The specific structure of the blood circuit is not fundamental to the present invention. Thus, with reference to FIG. 1, a brief description of a possible embodiment of a blood circuit is made, which is however provided purely by way of non-limiting example. The hydraulic circuit may further comprise one or more elements configured to prevent fluid flow through one or more lines. As shown in FIG. 1, the apparatus 1 may include a (venous) clamp 37 configured to receive a portion of the blood return line 30 and configured to clamp (e.g. close) fluid flow through the blood return line 30, in particular proximal to the second end 30-2 of the blood return line 30. Similarly, though not shown in FIG. 1 (see FIGS. 3B, 3C instead), the apparatus 1 may further include an (arterial) clamp 27 configured to receive a portion of the blood removal line 20 and configured to clamp (e.g. close) fluid flow through the blood removal line 20, in particular proximal to the first end 20-1 of the blood removal line 20. In some embodiments, apparatus 1 may include one or more tube retaining elements configured to receive, retain, and/or otherwise keep in place portions, sections, or tracts of one or more fluid lines (e.g. lines 20, 30, 40, 40b 50, 60, 70, 70b). Such tube retaining elements may include corresponding clamping mechanisms or valves or other actuators configured to control (e.g. prevent, enable, restrict, regulate) fluid flow through the respective portions, sections, or tracts of fluid lines. The one or more elements (e.g. 27, 37) configured to control fluid flow and/or tube retaining elements may be controlled, by the control unit 80, to clamp (e.g. close) the blood return line 30 if, for example, the blood return to the vascular access has to be halted during a rinse-back procedure which requires to block flow in certain lines/tracts or directions, and/or in emergency situations or for safety reasons. Each one of the pumps included in the extracorporeal blood treatment apparatus 1, for example pumps 22 and 72, may comprise a positive displacement pump, such as a peristaltic pump. In the example of FIG. 1, blood pump 22 and replacement pump 72 each include a peristaltic pump. Peristaltic pumps generally operate on a respective pump tube tract (e.g. 22t, 42t, 52t, 62t, 72t) configured to operably connect with the respective pump (e.g. 22, 42, 52, 62, 72) such that pump motion (e.g. rotation) is transferred onto the pump tube tract, thereby moving a respective fluid along the respective pump tube tract and, thus, through the respective line or lines (e.g. 20, 40, 40b, 50, 60, 70, 70b) as well as other components (e.g. treatment unit 10, blood warmer 33, and/or air separator 35). The hydraulic circuit may further comprise a post-infusion line 70b, which branches off from the pre-infusion line 70 at a branch 73. The branch typically includes a flow controller (e.g. one or more valves or a clamp mechanism) configured to selectively enable fluid flow either through the pre-infusion line 70 or through the post infusion line 70b. In detail, replacement pump 72, active on the pre-infusion line 70 and arranged upstream branch 73 (with respect to fluid flow from the replacement fluid container 78 towards branch 73), is configured to supply replacement fluid from the replacement fluid container 78 to the blood circuit 20, 30. Branch 73 (including, e.g., a flow controller, valve(s), and/or clamp(s); see above) is configured to selectively allow supply of replacement fluid from the replacement fluid container 78 through the pre-infusion line 70 or through the post-infusion line 70b. In case of pre-infusion, the replacement fluid is introduced into the blood removal line 20 at a first pre-infusion site 20-3b upstream the treatment unit 10 (with respect to fluid flow from the first end 20-1 of the blood removal line 20 to the second end 20-2 of the blood removal line 20). In case of post-infusion, the replacement fluid is introduced into the blood return line 30 downstream from the treatment unit 10 (with respect to fluid flow from the first end 30-1 of the blood return line 30 to the second end 30-2 of the blood return line 30). In some embodiments, the second end 70b-2 of the post-infusion line 70b is connected to the blood return line 30 via an air separator 35, such that replacement fluid can be introduced into the fluid flowing through the blood return line 30 within the air separator 35, which may improve mixing of the fluids and/or the effectiveness of the air separator 35 in separating gas/air from the fluid flowing there-through. As illustrated in FIG. 1, different sections of the hydraulic circuit exhibit corresponding (internal) volumes for processed fluids, which have to be taken into account when focusing on blood return. Volume V1 denotes a first volume in a first section of the blood removal line 20, between the first end 20-1 of the blood removal line 20 (e.g. patient access, catheter access) and a second pre-infusion site 20-3a upstream the blood pump 22 (see PBP pre-infusion described further below). Volume V2 denotes a second volume in a second section of the blood removal line 20 between the second pre-infusion site 20-3a and the first pre-infusion site 20-3b downstream from the blood pump 22 (and upstream from the treatment unit 10). Volume V2 includes the volume of the blood pump tract 22t. Volume V3 denotes a third volume in a third section of the blood removal line 20 between the first pre-infusion site 20-3b and the second end 20-2 of the blood removal line 20. Volume V4 denotes a fourth volume of the first chamber of the treatment unit 10. Volume V5 denotes a fifth volume in a first section of the blood return line 30 between the first end 30-1 of the blood return line 30 and an inlet connector 30-3a of the blood warmer 33. The blood warmer, if present, also includes an internal volume denoted as $V_{33}$. Notably other devices might be selectively included in the blood circuit, such as a gas exchanger for $CO_2$ removal (i.e. to perform $ECCO_2R$ therapies) and/or an adsorption device; these devices, if present, also includes respective volumes. In the following description volume $V_{33}$ is referred to the blood warmer, however this should not be considered as limiting. Volume V6 denotes a sixth volume in the blood return line 30 between an outlet connector 30-3b of the blood warmer 33 and the second end 30-2 of the blood return line 30. Unless otherwise specified, volume V6 includes a volume $V_{35}$ of fluid present in air separator 35. Table 1 shows some example values for typical volumes V1 to V6, depending upon the type of hydraulic circuit used. Typical volumes of blood circuit section/example of circuit for application in adults are in the following table

| | Circuit section | | | | | | |
|---|---|---|---|---|---|---|---|
| | V1 | V2 | V3 | V4 | V5 | V6 | V33 |
| Volume (ml) | 3 | 40 | 5 | 80 | 5 | 35 | 25 |

The hydraulic circuit may further comprise a second dialysate line 40b, which branches off from the dialysate line 40 at a branch 43. The branch typically includes a flow controller (e.g. one or more valves or a clamp mechanism) configured to selectively enable fluid flow either (solely) through the dialysate line 40 (i.e. from the first end 40-1 thereof to the second end 40-2 thereof) or, alternatively, through the first part of the dialysate line 40 up to branch 43 and further through second dialysate line 40b and post infusion line 70b (i.e. from the first end of dialysate line 40 to branch 43, through second dialysate line 40b and post infusion line 70b, to the second end 70b-2 of post infusion line 70b). In detail, dialysate pump 42, active on the dialysate line 40 and arranged upstream the branch 43 (with respect to fluid flow from the dialysate container 48 towards branch 43), is configured to supply dialysate from the dialysate container 48 to treatment unit 10. Branch 43 (including, e.g., a flow controller, valve(s), and/or clamp(s); see above) is configured to selectively allow supply of dialysate from dialysate container 48 through the dialysate line 40 or through the second dialysate line 40b, and, subsequently further through post infusion line 70b.

Figure 2:
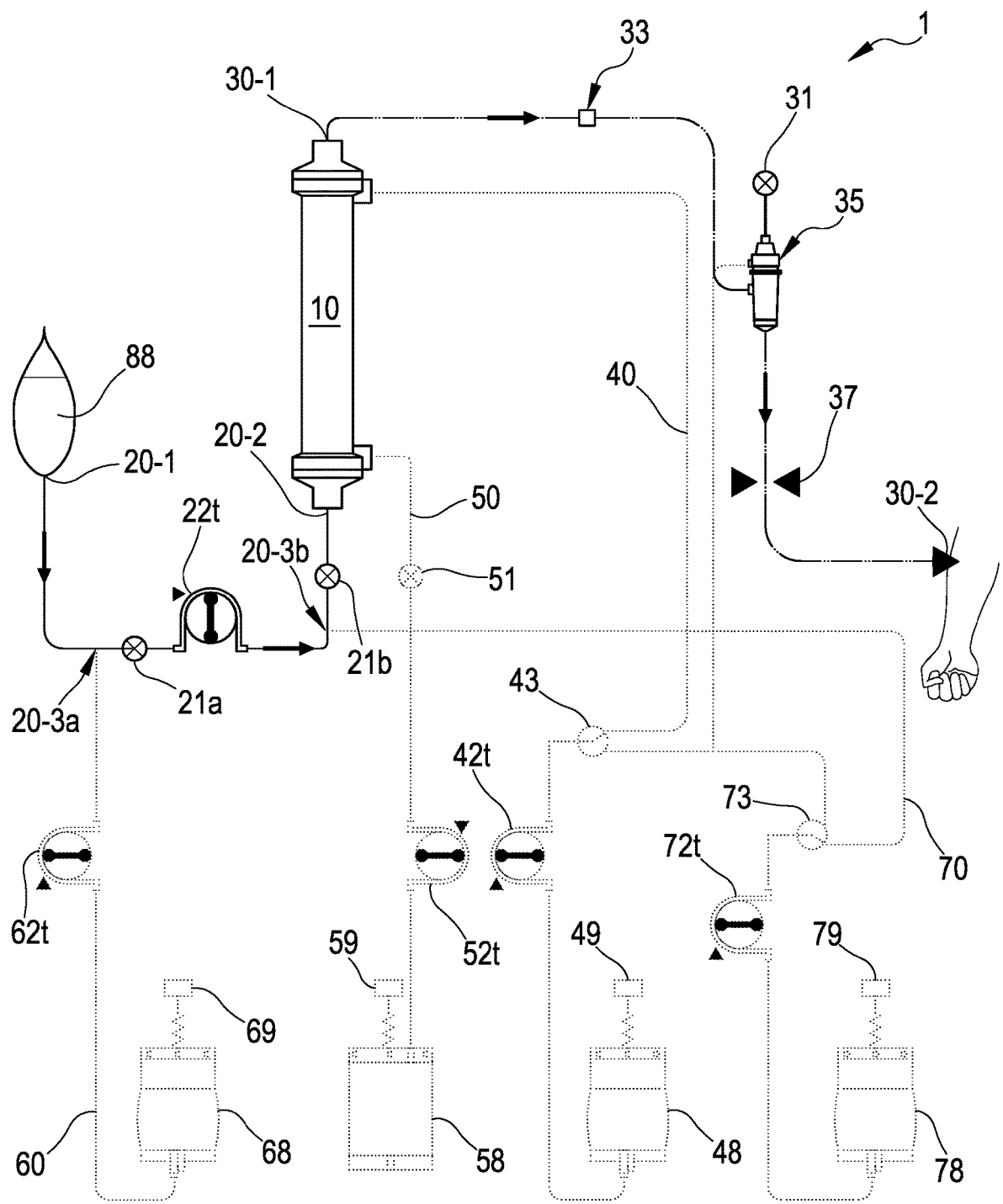
FIG. 2 schematically illustrates a configuration of an extracorporeal blood circuit during a known process for rinsing back blood from the extracorporeal blood circuit to a patient.
Figure 3B:
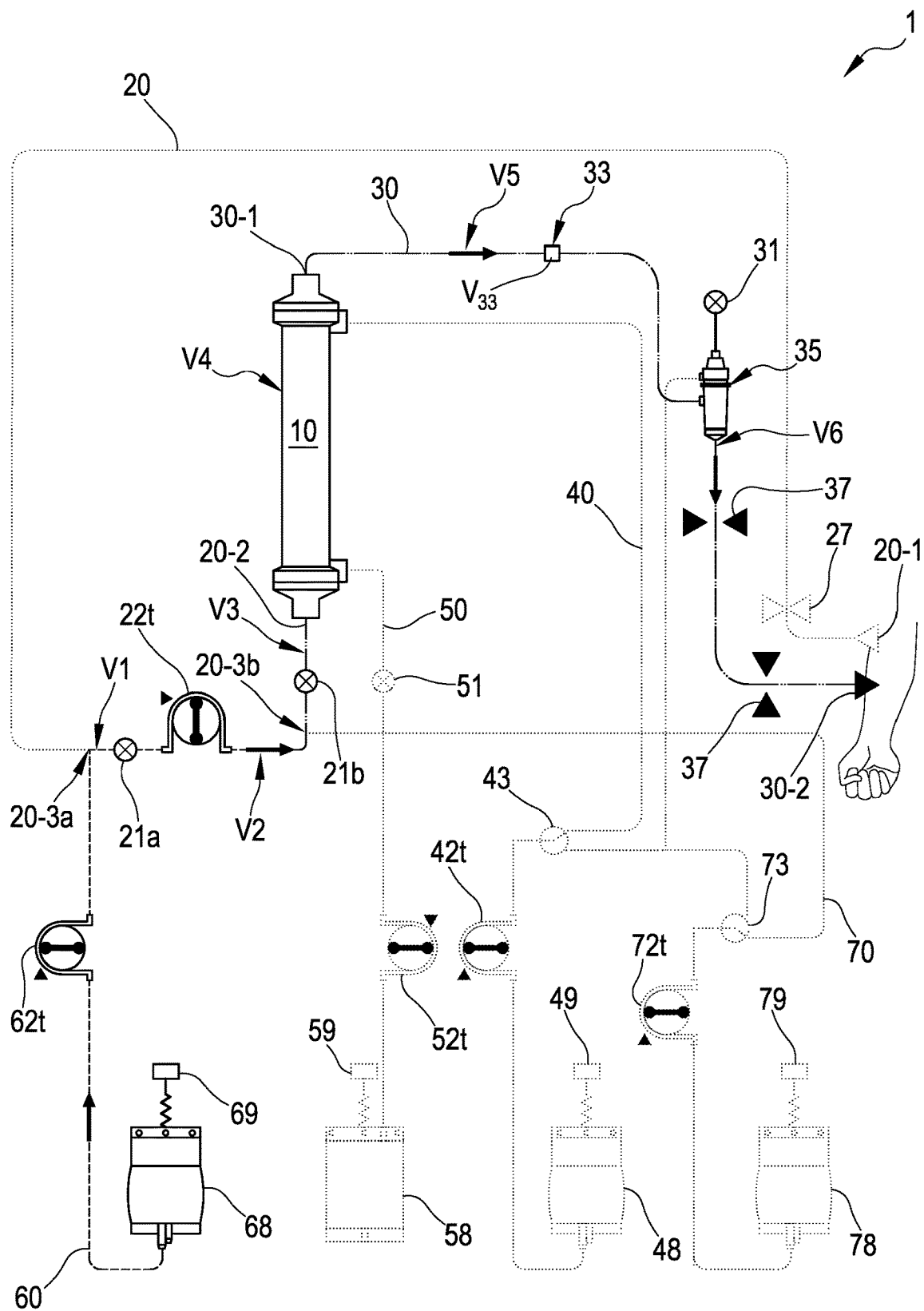
FIG. 3B schematically illustrates a first phase of the process for rinsing back blood from an extracorporeal blood circuit to a patient in accordance with the first embodiment of the present invention.
Figure 3C:
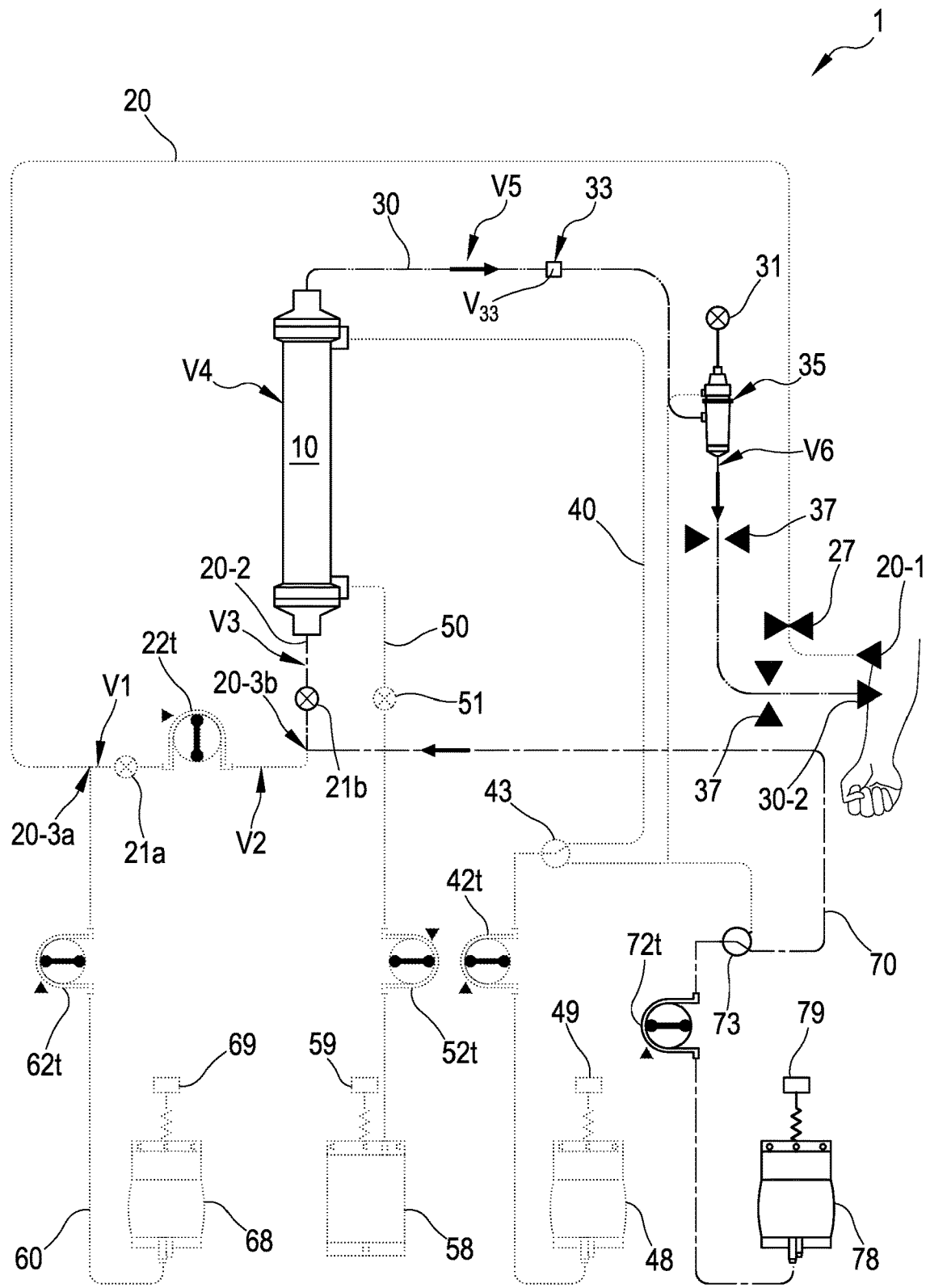
FIG. 3C schematically illustrates a second phase of the process for rinsing back blood from an extracorporeal blood circuit to a patient in accordance with the first embodiment of the present invention.
Figure 3D:
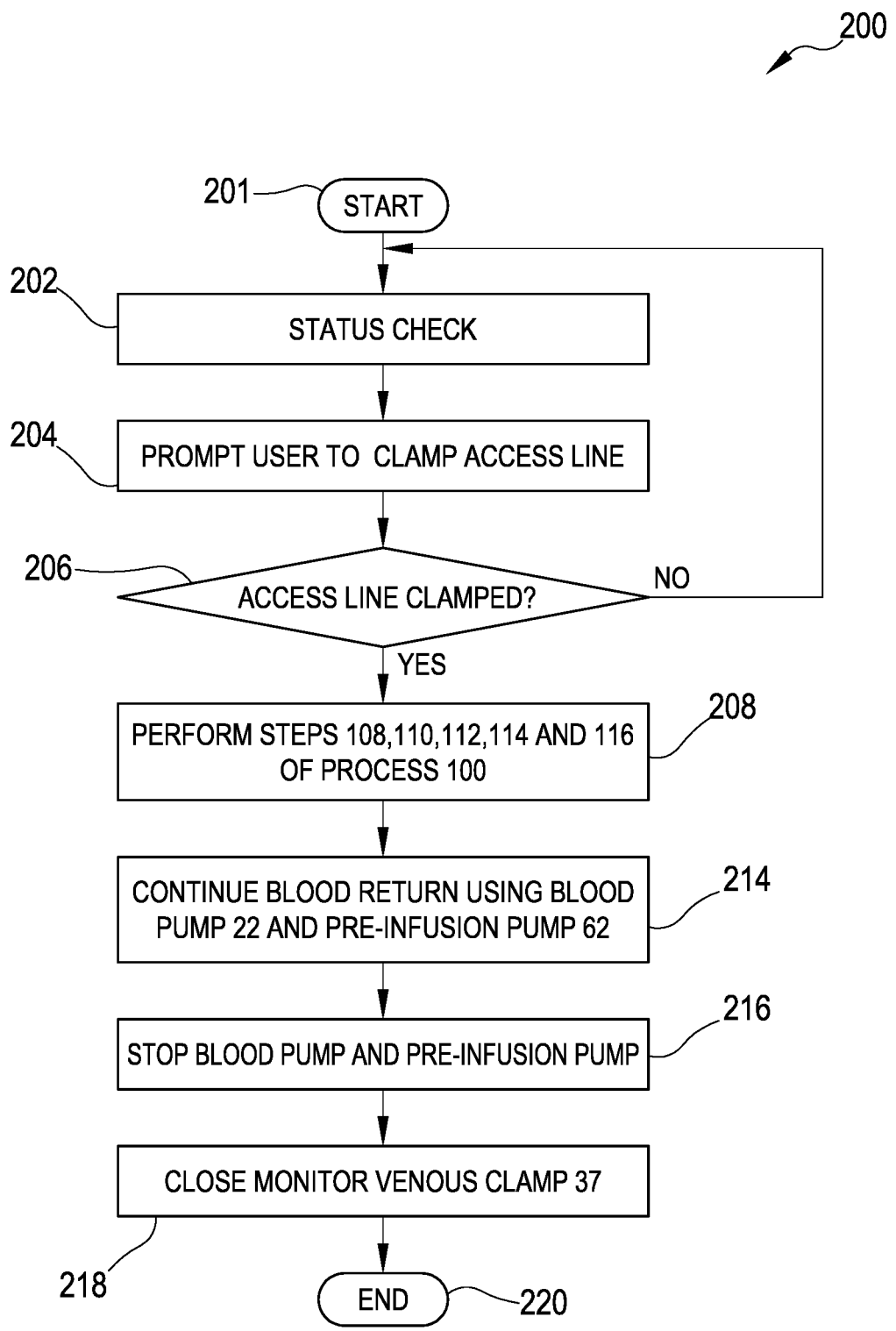
FIG. 3D shows a flow chart of a process for rinsing back blood from an extracorporeal blood circuit to a patient in accordance with a second embodiment of the present invention.

FIG. 2 schematically illustrates a configuration of an extracorporeal blood circuit during a known process for rinsing back blood from the extracorporeal blood circuit to a patient. The known process is described based on the hydraulic circuit shown in FIG. 1, but is typically applicable to a number of similar hydraulic circuits, which can, however, be structurally different from the hydraulic circuit shown in FIG. 1. The known process includes several aseptic and non-aseptic steps. The blood return procedure is performed using the blood pump 22 only and by connecting the first end 20-1 of the blood removal line 20 to a bag 88 containing infusion fluid. In preparation for the known return procedure, an infusion fluid bag 88 containing infusion fluid has to be provided/prepared. In first and second steps (non-aseptic), the patient access and the blood removal line 20 near the first end 20-1 thereof have to be closed, for example by clamping the line 20 proximate the first end 20-1 and by clamping the access catheter of the patient. In third and fourth steps (aseptic), the blood removal line 20 has to be disconnected from the catheter and the first end 20-1 of the blood removal line 20 has to be connected to the infusion fluid bag 88. Steps three and four are aseptic steps, which means that the operator performing these steps is required to follow a strict protocol ensuring that these steps are performed in line with regulations of patient care. In a fifth step (non-aseptic), fluid communication from bag 88 to line 20 is enabled (e.g. by breaking a sealing pin on bag 88). In a sixth step (non-aseptic), the blood removal line 20 is unclamped (proximate the first end 20-1 thereof; see above). In a seventh step (non-aseptic), the blood return procedure is started by controlling the blood pump 22 to convey fluid contained in the blood removal line 20 towards the second end 30-2 of the blood return line. During this step, the infusion fluid from bag 88 gradually replaces the fluid in the blood circuit. In some examples, the volume of infusion fluid replacing the fluid in the blood circuit has to be determined by the operator performing the return procedure, who is also required to initiate, oversee, and stop the return process depending on the progress thereof. In other examples, the blood treatment apparatus may determine an amount of infusion fluid based on the hydraulic circuit used, in which cases the operator may still have to perform the return process as described above, for example by pressing a corresponding control key on the graphical user interface of the apparatus. In an eighth step (non-aseptic), the blood return procedure is stopped by controlling the blood pump 22 to stop. In a ninth step (non-aseptic), the return catheter is closed (e.g. clamped). In a tenth step (non-aseptic), fluid flow through the blood return line 30 is prevented, for example by closing (e.g. clamping) the blood return line 30 proximate its second end 30-2. In an eleventh step (aseptic), the return catheter is disconnected from the blood return line 30, which again is an aseptic step (see steps three and four above). It has been found that, using the known process, neither the flow rate during the blood return procedure nor the use of back-filtration can lead to a significant improvement in blood recovery. Instead, the volume of fluid returned was found to be the most relevant parameter in blood recovery, facilitating recovery of up to 85% when the returned volume was equal to the nominal volume of the blood circuit. Further, the necessity of aseptic and non-aseptic steps complicates the blood return process. This issue of aseptic and non-aseptic steps is even more relevant in CRRT systems, as described above. The blood return procedure in accordance with embodiments of the present invention focuses on several issues associated with known procedures. The return procedure is designed to use, as return fluid, the fluid from bags already connected to the CRRT system and previously used for treating the patient (e.g. being substitution fluid and/or PBP replacement fluid such as citrate compositions, such as the fluids included in pre-infusion fluid container 68, dialysis fluid container 48 and/or replacement fluid container 78). This allows the blood return procedure to start, if necessary, basically immediately, without prior preparation and connection of an additional bag of infusion fluid, albeit depending on a residual amount of fluid in such bags already connected to the CRRT system. Further, the blood return procedure can be performed with both the blood removal line and the blood return line remaining connected to the patient vascular system, such that an operator or nurse does not have to perform any non-aseptic actions. This allows for the blood return procedure to start or be started very quickly, thus substantially reducing the risks of (further) complications occurring before or during the blood return procedure (e.g. clotting, alarm(s), etc.). The volume of return fluid required to achieve a comparable blood recovery of about 80% is less than the volume of the blood circuit of a CRRT system (e.g. less than 200 ml for a circuit for adult patient/circuit without blood warmer) and corresponds to less than $\kappa$% of the capacity of a typical 5-liter fluid bag. In the vast majority of cases, therefore, there should be sufficient residual fluid amount in the connected bag or bags in order to fully perform the blood return procedure (e.g. to return at least 80% of blood). Even in cases where the residual fluid amount is less than the volume ideally required, it is much better to perform a partial blood return rather than no blood return at all. In an example in which only 100 ml of residual fluid is available, which should only occur in very few cases, see above, this would still enable a blood recovery of about 50% of the volume contained in the blood circuit. It has been found that in CRRT, statistically, successful blood recovery (e.g., ratio of volume of fluid used for blood return to the circuit blood volume of at least 0.5) is achieved merely in about 43% of cases. However, in a higher number of cases (about 50% of cases), no blood has been recovered at all. Additionally, the rinse back procedures here-below described provides to the operator the possibility to stop and resume the blood return process at any time, as well as aborting it before full completion, depending on the circumstances. FIG. 3A shows a flow chart of a process for rinsing back blood from an extracorporeal blood circuit to a patient in accordance with a first embodiment of the present invention. Blood return process 100 generally includes rinsing back blood to a patient through the blood return line 30 using fluid from the PBP fluid container 68 and the replacement fluid container 78. Blood return process 100 is described with reference to FIGS. 3B and 3C. FIG. 3B schematically illustrates a first phase of the process 100 for rinsing back blood from an extracorporeal blood circuit to a patient in accordance with the first embodiment of the present invention (see, in particular, steps 110 and 112 in FIG. 3A). FIG. 3C schematically illustrates a second phase of the process 100 for rinsing back blood from an extracorporeal blood circuit to a patient in accordance with the first embodiment of the present invention (see, in particular, steps 114 and 116 in FIG. 3A). In both FIGS. 3B and 3C, dotted lines and components indicate components not involved in the respective step or phase of the rinse-back procedure. Blood return process 100 starts at step 101, in which the blood pump 22 is stopped, e.g. at the end of the treatment phase. In step 102, the requirements for performing process 100 are evaluated in a status check. This may include making sure that the fluid volume present in replacement fluid container 78 is greater than $\alpha*(V3+V4+V5+V6+V_{33})$, with a being e.g. 1.0 ($\alpha$ is an operator settable parameter to determine the percentage of extracorporeal blood in volume $V3+V4+V5+V6+V_{33}$ which is desired to restitute—$\alpha=1$ means restituting 100% of extracorporeal blood in volume $V3+V4+V5+V6+V_{33}$), and that the fluid volume present in the PBP pre-infusion container 68 is greater than or equal to V2. For the applicability of process 100 it is not relevant the fluid content, e.g. whether the PBP pre-infusion container 68 contains PBP solution having a low or a high concentration of citrate. The maximum usable fluid volume of PBP fluid is V2. The target return volume (using replacement solution) is $1.0*(V3+V5+V6+V_{33})$. The entire restitution volume (i.e. $V2+1.0*(V3+V5+V6+V_{33})$), thus is almost identical (e.g. about 99%) of the blood circuit volume. If the requirements are not met, process 100 may still be performed in order to rinse back at least some of the blood present in the blood circuit (see above). In some cases, minimum requirements may be defined, which determine whether the rinse-back procedure 100 is fully, partially, or not at all performed. For example, if the replacement fluid container 78 is empty, the rinse back procedure may be aborted. If the requirements are met, the blood return line 30 is closed proximate its second end 30-2. In step 104, the user is prompted to clamp the blood removal line 20 proximate the first end 20-1 thereof and in step 106 the successful clamping of the blood removal line 30 is checked and verified. If the clamping is not achieved or cannot be verified, the process 100 is started over, returning back to step 101. If the successful clamping of the blood removal line is verified, then the process continues at step 108, in which fluid flow through the blood return line 30 is enabled, in the present embodiment by opening venous clamp 37. In step 110, both the PBP fluid pump 62 and the blood pump 22 are controlled to return fluid (e.g. blood or PBP solution) from section V2 of the blood removal line 20 as shown in FIG. 3B. In this step, the flow rate of both pumps 22 and 62 is synchronized and controlled based e.g. on monitoring the access pressure. Further, venous pressure is monitored in order to detect an occlusion or clotting in the blood circuit. The volume of PBP fluid pumped into the blood circuit is monitored and controlled to not exceed V2 and may be determined based on the rotation of the PBP fluid pump 62 and/or based the weight of the pre-infusion fluid container 68 (e.g. a change in weight thereof) measured with a pre-infusion fluid scale 69. In step 112, the blood pump 22 and the PBP fluid pump 62 are stopped when the volume returned to the blood circuit reaches V2. In step 114, the replacement fluid pump 72 is controlled to return blood downstream from the pre-infusion site 20-3b as shown in FIG. 3C. The volume returned to the blood circuit may be determined either based on the rotation of the replacement fluid pump 72 and/or based on the weight of the replacement fluid container 78 (e.g. a change in weight thereof). Again, venous pressure is monitored in order to detect an occlusion or clotting in the blood circuit. In step 116, the replacement fluid pump 72 is stopped when the volume returned to the blood circuit reaches $V3+V4+V5+V6+V_{33}$. Subsequently, in step 118, the venous clamp 37 is closed and the process 100 ends at step 120. During all steps of the rinse-back procedure, the clamp 27 on the blood removal line 20 is closed to avoid any blood flow directed towards the arterial access to the patient (i.e. towards the first end of blood removal line 20-1). Blood return process 100 in accordance with the first embodiment of the invention allows for the return of substantially the entire volume of the blood circuit ($V2+V3+V4+V5+V6+V_{33}$; corresponding to about 99% of an adult set). The effectiveness of process 100 is determined by the theoretical effectiveness associated to the value a multiplied with the partial volume (see above). If, in an example, $\alpha=1.0$, the restitution volume is almost equal (99%) to the blood circuit blood volume and the effectiveness of the return process is about 83/84/84% for an LF set/an HF set/an HF set with blood warmer. Not taking into consideration any delays due to switching times potentially necessary between different process steps, the duration of process 100 is largely proportional to the return flow-rate. The duration of process 100 in an example based on an adult set including a blood warmer is about 2:40 minutes at a flow rate of 100 ml/min and a blood return effectiveness of 84%. Additionally, should no fluid be present in the pre-infusion fluid container 68, the rinse-back procedure of embodiment 1 may be equally used. Of course the steps 110 and 112 are not performed (i.e. blood in volume V2 is not restituted to the patient) and the procedure makes use of the medical fluid in the replacement container 78 only. FIG. 3D shows a flow chart of a process for rinsing back blood from an extracorporeal blood circuit to a patient in accordance with a second embodiment of the present invention. Blood return process 200 generally includes rinsing back blood to a patient through the blood return line 30 using fluid from the PBP fluid container 68 and the replacement fluid container 78. In contrast to blood return process 100, blood return process 200 allows for returning to rinse-back using PBP fluid in case the residual volume of replacement fluid is not sufficient for reaching a target return volume. Though not exclusively, the user or the control unit 80 (e.g. automatically) selects a rinse-back procedure according to the first embodiment whenever the fluid volume in the replacement container 78 is sufficient, i.e. above the mentioned pre-defined volume equal to $\alpha*(V3+V4+V5+V6+V_{33})$. When the fluid volume is less than the pre-defined volume, a substantially complete rinse-back procedure may be achieved using a procedure in accordance with the second embodiment, which is described in the following. Blood return process 200 of the second embodiment is also described with reference to FIGS. 3B and 3C. FIG. 3B schematically illustrates a first phase of the process 200 for rinsing back blood from an extracorporeal blood circuit to a patient in accordance with the second embodiment of the present invention. FIG. 3C schematically illustrates a second phase of the process 200 for rinsing back blood from an extracorporeal blood circuit to a patient in accordance with the second embodiment of the present invention. The first and second phases of process 200 largely correspond to steps 108 to 116 as described above and a shown in FIG. 3A (see corresponding step 208 in FIG. 3D). Process 200 for rinsing back blood from an extracorporeal blood circuit to a patient in accordance with the second embodiment of the present invention further includes a third phase (see steps 214 and 216 in FIG. 3D), which is also illustrated in FIG. 3B. Blood return process 200 starts at step 201 in which blood pump is stopped. In step 202, the requirements for performing process 200 are evaluated in a status check. This may include checking whether the fluid volume present in replacement fluid container 78 is greater than $\alpha*(V3+V4+V5+V6+V_{33})$ or not, with a being an operator prescription, whose typical value lies in the range between 0.75 and 1. In case the fluid volume is lower than the necessary fluid for the previously describe rinse-back procedure ($1^{st}$ embodiment), the status check may additionally include controlling that the fluid volume present in the PBP pre-infusion container 68 is much greater than V2 (e.g. PBP Volume>>V2). For the applicability of process 200 it is not relevant whether the PBP pre-infusion container 68 contains PBP solution having a low or a high concentration of citrate. However, the maximum usable fluid volume of PBP fluid depends on the citrate content. If the PBP solution is known to contain high citrate content or is unknown, the target return volume (using PBP solution) is $V2+\alpha*(V3+V5+V6+V_{33})$, wherein the maximum allowable value for a is set at 0.75; this volume excludes the filter volume according to possible clotting of the filter. The reason for reducing the maximum returnable blood, is patient safety. Indeed, in case citrate is present, additional constraints should be considered. In more detail, the design should be such that it secures that the total amount of citrate (i.e. citrate fluid volume from PBP container 68×citrate concentration) that might reach the patient is not excessive. This can be defined respectively to patient body weight and/or mean PBP flow rate used during blood treatment. Of course, definition of volume reaching patient shall consider worst case scenario where a significant fraction of the membrane filter is also clotted (meaning that actual volume V4 to rinse is much smaller than 'nominal' V4 volume). In such a case, an additional constrain based on mean PBP flow rate during previous patient blood treatment could be imposed, such as that no more than the equivalent of 10 min of mean PBP flow rate should be infused into the patient during the entire rinse-back procedure. In this respect, the control unit 80 stores PBP flow rate applied during treatment (e.g., the flow rate of citrate solution over time is measured by the control unit 80 and stored in a memory during treatment or the mean PBP flow rate applied during treatment is received as an input before rinse-back procedure); during the rinse-back procedure, the control unit 80 is configured to infuse into the patient less than the equivalent of 10 min of mean PBP flow rate. In other terms a maximum PBP volume form container 68 is calculated based on the mentioned relationship and no more than the calculated volume from PBP container 68 can be used for the rinse-back procedure, this allowing to infuse no more than the equivalent of 10 min of mean PBP flow rate. If the PBP solution is known to contain low citrate content, the target return volume (using PBP solution) is $V2+\alpha*(V3+V4+V5+V6+V_{33})$; again $\alpha$ is settable to a maximum value of 0.75, however volume V4 is taken into consideration. In both cases an alternative target return volume is determined as V2+a predetermined volume based on a previous therapy PBP setting. The second embodiment requires that the blood pump 22 is stopped and the blood return line 30 is closed proximate its second end 30-2. In step 204, the user is prompted to clamp the blood removal line 20 proximate the first end 20-1 thereof and in step 206 the successful clamping of the blood removal line 30 is checked and verified. If the clamping is not verified, the process 200 is started over, returning back to step 201. If the successful clamping of the blood removal line is verified, then the process continues at step 208, in which the same steps are performed as in steps 108, 110, 112, 114, and 116, as described with reference to process 100 above. The process 200 continues at step 214 in which both the PBP fluid pump 62 and the blood pump 22 are controlled to return fluid (e.g. PBP solution) from PBP fluid container 68 to the blood removal line 20 and further, as shown in FIG. 3B. This second rinse-back step using the PBP fluid pump 62 and the blood pump 22 is continued until the sum of the fluid volume returned in sub-step 114 of step 208 and in step 214 reaches the target return volume. Again, the volume returned to the blood circuit may be determined either based on the rotation of the respective fluid pumps 22, 62, and 72 and/or based on the weight of the respective fluid containers 68 and 78 (e.g. a change in weight thereof). As described above, during rinse back the venous pressure is monitored in order to detect an occlusion or clotting in the blood circuit. In step 216, the PBP fluid pump 62 and blood pump 22 are stopped when the volume returned to the blood circuit has reached the target return volume. Subsequently, in step 218, the venous clamp 37 is closed and the process 200 ends at step 220. FIG. 4 shows a flow chart of a process for rinsing back blood from an extracorporeal blood circuit to a patient in accordance with a third embodiment of the present invention. Blood return process 300 generally includes rinsing back blood to a patient through the blood return line 30 only using fluid from the PBP fluid container 68. Blood return process 300 is described with reference to FIG. 3B. FIG. 3B schematically illustrates the process 300 for rinsing back blood from an extracorporeal blood circuit to a patient in accordance with the third embodiment of the present invention. Blood return process 300 starts at step 301 when blood pump is stopped. In step 302, the requirements for performing process 300 are evaluated in a status check. This may include making sure that the fluid volume present in PBP fluid container 68 is greater than $\alpha*(V2+V3+V4+V5+V6+V_{33})$, with a being set at a desired limit (e.g. 0.75). For the applicability of process 300 it is not relevant whether the PBP pre-infusion container 68 contains PBP solution having a low or a high concentration of citrate. However, the maximum usable fluid volume of PBP fluid depends on the citrate content. The return procedure making use of citrate solution from PBP bag (i.e. pre-infusion container 68) has the same constrains above described in respect to the second embodiment and again the apparatus determines the maximum usable fluid from pre-infusion container 68 that is usable without infusing an excessive citrate amount into the patient (e.g. the equivalent of 10 min of mean PBP flow rate). If the PBP solution is known to contain high citrate content or is unknown, the target return volume is $V2+0.75*(V3+V5+V6+V_{33})$, this volume excluding the filter volume V4 according to possible clotting of the filter. If the PBP solution is known to contain low citrate content, the target return volume is $V2+0.75*(V3+V4+V5+V6+V_{33})$. In both cases an alternative target return volume is determined as V2+a predetermined volume of a previous therapy PBP setting. If the requirements are not met, in particular if the volume present in the PBP fluid container is not greater than $\alpha*(V2+V3+V4+V5+V6+V_{33})$, process 300 may still be performed in order to rinse back at least some of the blood present in the blood circuit (see above). Again, in some cases, minimum requirements may be defined, which determine whether the rinse-back procedure 300 is fully, partially, or not at all performed. If the requirements are met the blood pump 22 is stopped and the blood return line 30 is closed proximate its second end 30-2. In step 304, the user is prompted to clamp the blood removal line 20 proximate the first end 20-1 thereof and in step 306 the successful clamping of the blood removal line 30 is checked and verified. If the clamping is not verified, the process 300 is started over, returning back to step 301. If the successful clamping of the blood removal line is verified, then the process continues at step 308, in which the PBP fluid pump 62 and the blood pump 22 are controlled to return fluid downstream from the second pre-infusion site 20-3a as shown in FIG. 3B. The volume returned to the blood circuit may be determined either based on the rotation of the PBP fluid pump 62 (and/or the blood pump 22) and/or based on the weight of the PBP fluid container 68 (e.g. a change in weight thereof). Again, venous pressure is monitored in order to detect an occlusion or clotting in the blood circuit. In step 312, the PBP fluid pump 62 and the blood pump 22 are stopped when the volume returned to the blood circuit reaches $\alpha*(V2+V3+V4+V5+V6+V_{33})$. In case this volume exceeds the maximum volume infusible from pre-infusion container 68 due to the citrate mentioned constraints, the rinse-back procedure is stopped as soon as the maximum infusible fluid volume is reached. Subsequently, in step 314, the venous clamp 37 is closed and the process 300 ends at step 316. The duration of process 300 is directly proportional to the blood flow-rate during the return phase and to the volume of the returned fluid.

Figure 5A:
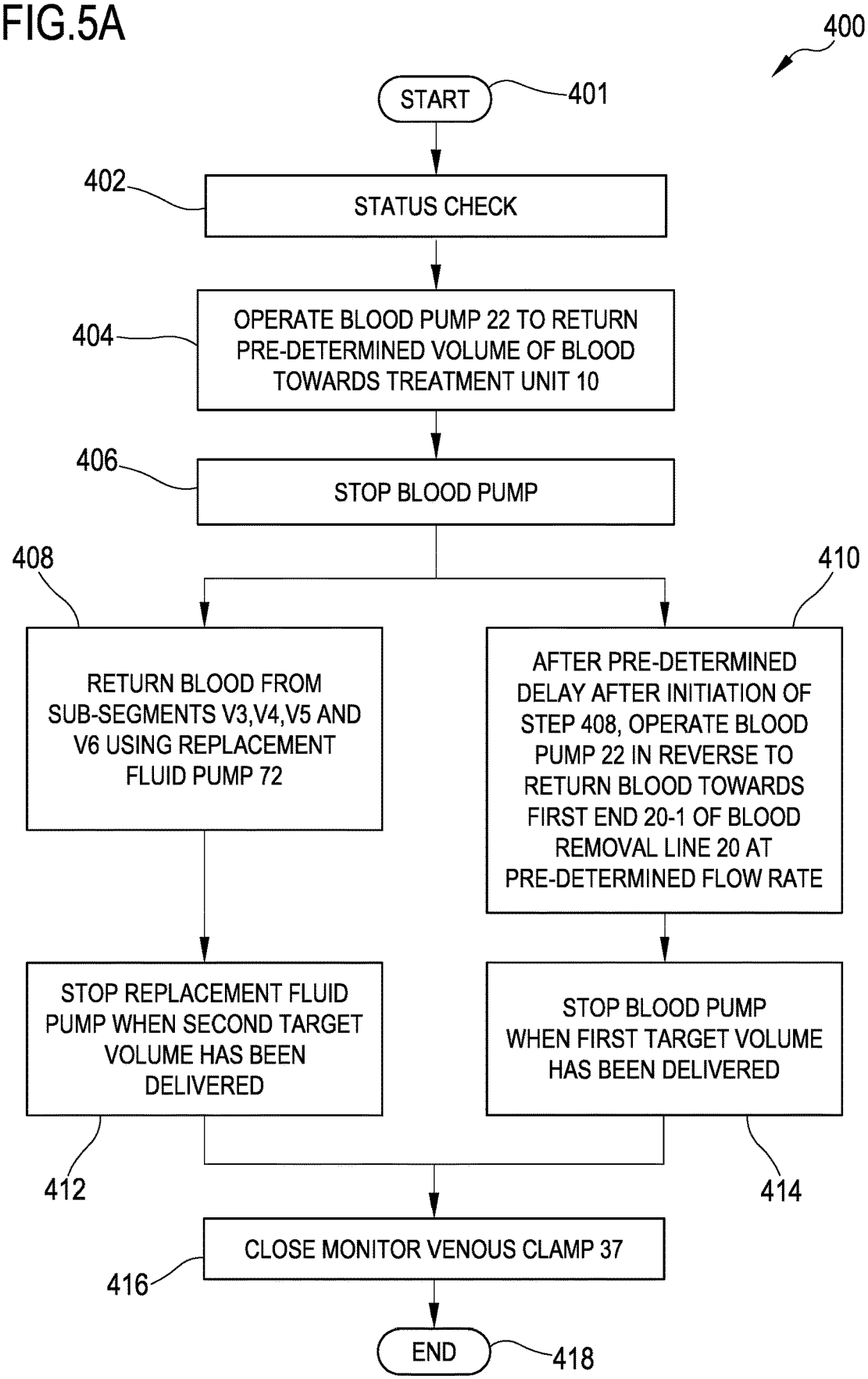
FIG. 5A shows a flow chart of a process for rinsing back blood from an extracorporeal blood circuit to a patient in accordance with a fourth embodiment of the present invention.
Figure 5B:
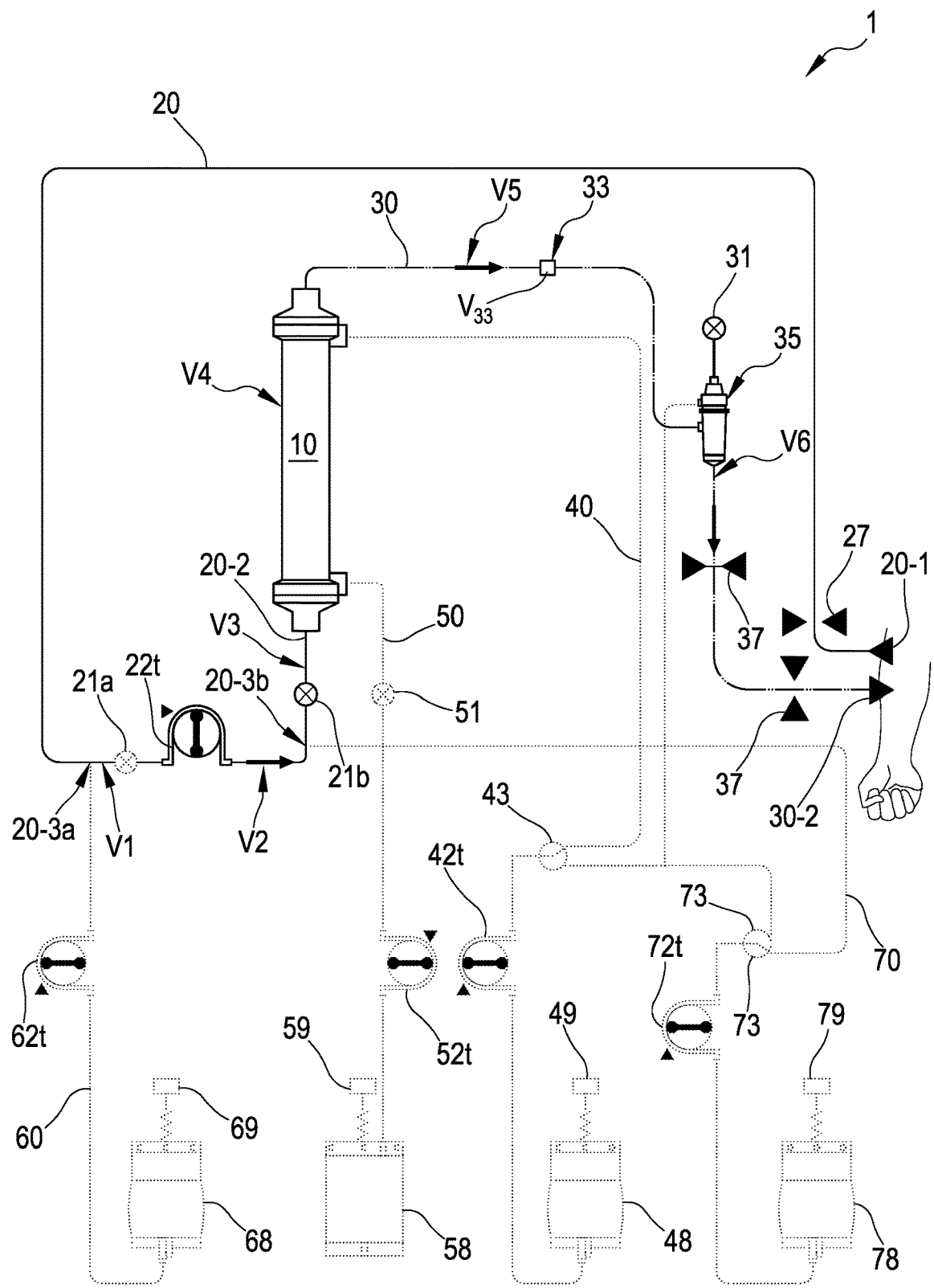
FIG. 5B schematically illustrates a first phase of the process for rinsing back blood from an extracorporeal blood circuit to a patient in accordance with the fourth embodiment of the present invention.
Figure 5C:
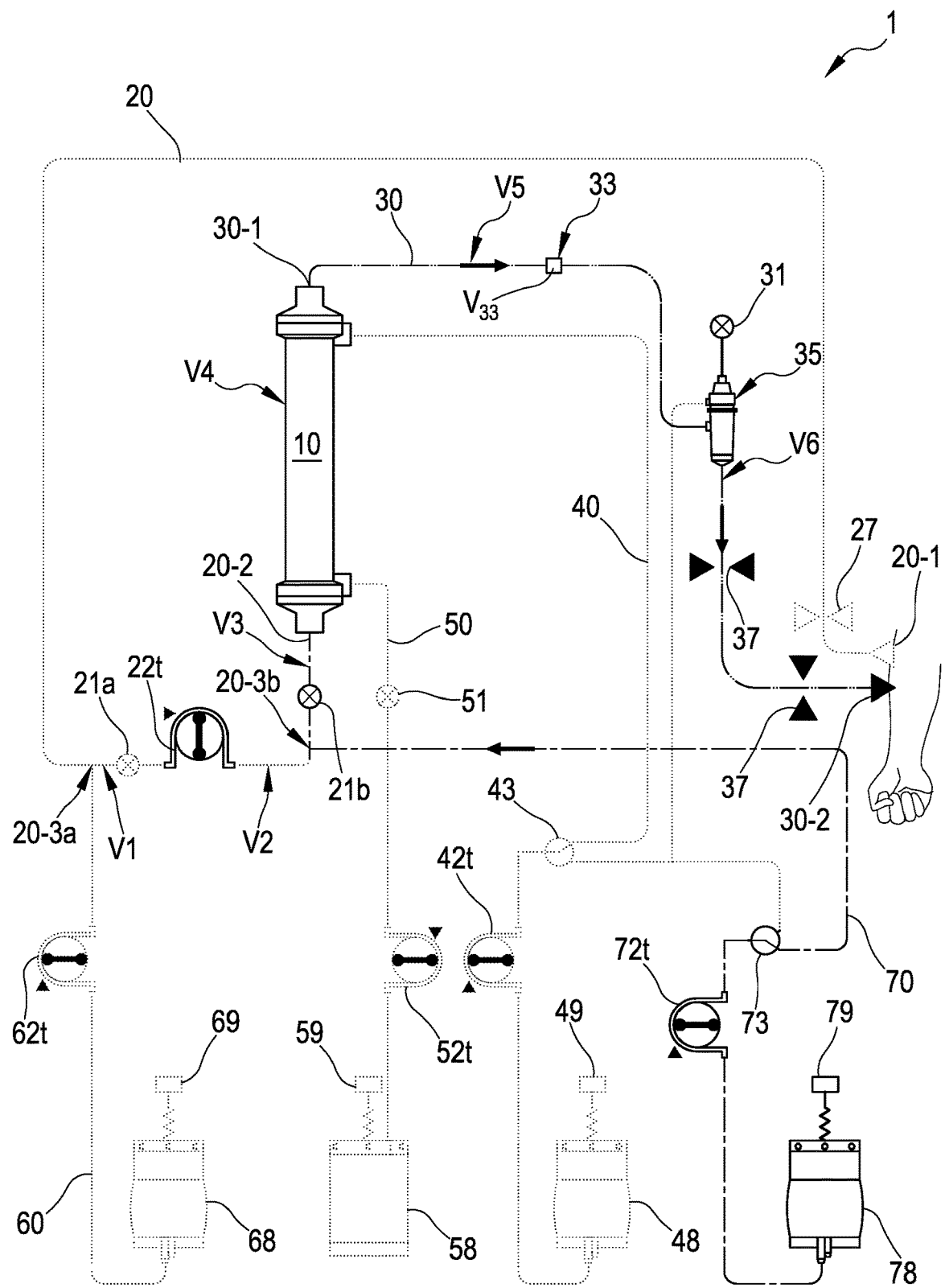
FIG. 5C schematically illustrates a second phase of the process for rinsing back blood from an extracorporeal blood circuit to a patient in accordance with the fourth embodiment of the present invention.
Figure 5D:
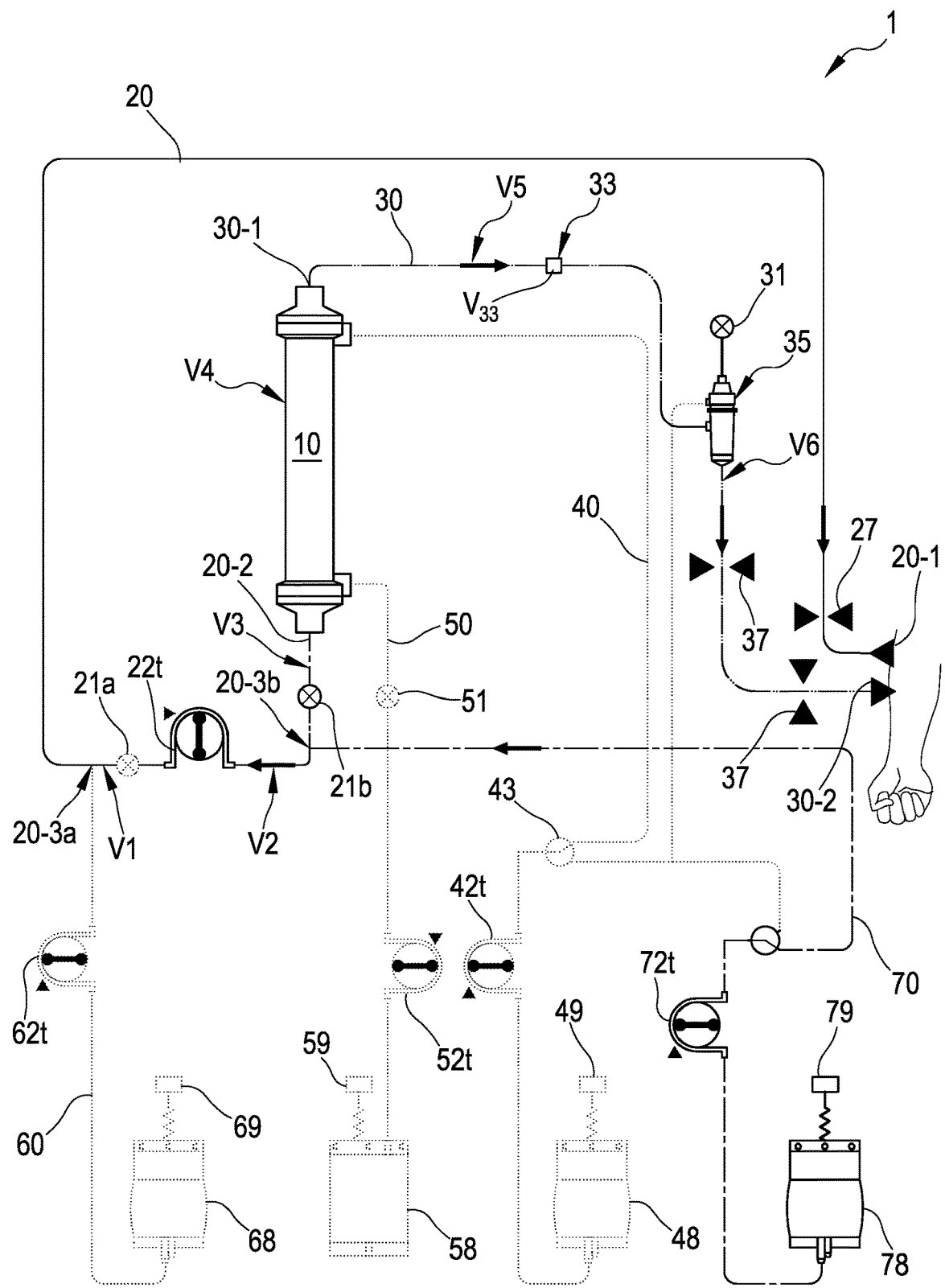
FIG. 5D schematically illustrates a third phase of the process for rinsing back blood from an extracorporeal blood circuit to a patient in accordance with the fourth embodiment of the present invention.
Figure 5E:
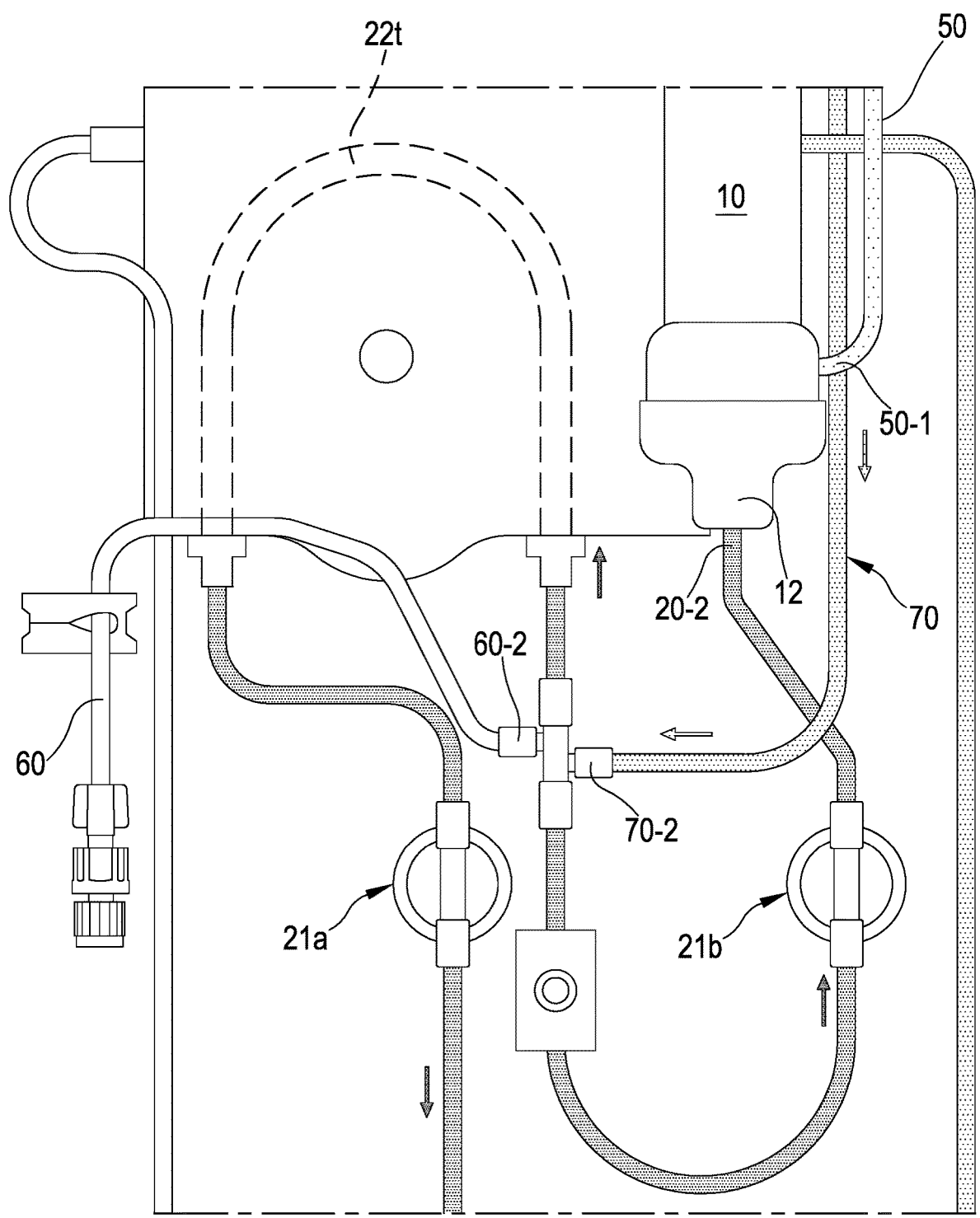
FIG. 5E schematically represents a portion of the extracorporeal blood treatment apparatus in accordance with embodiments of the present invention.
Figure 6:
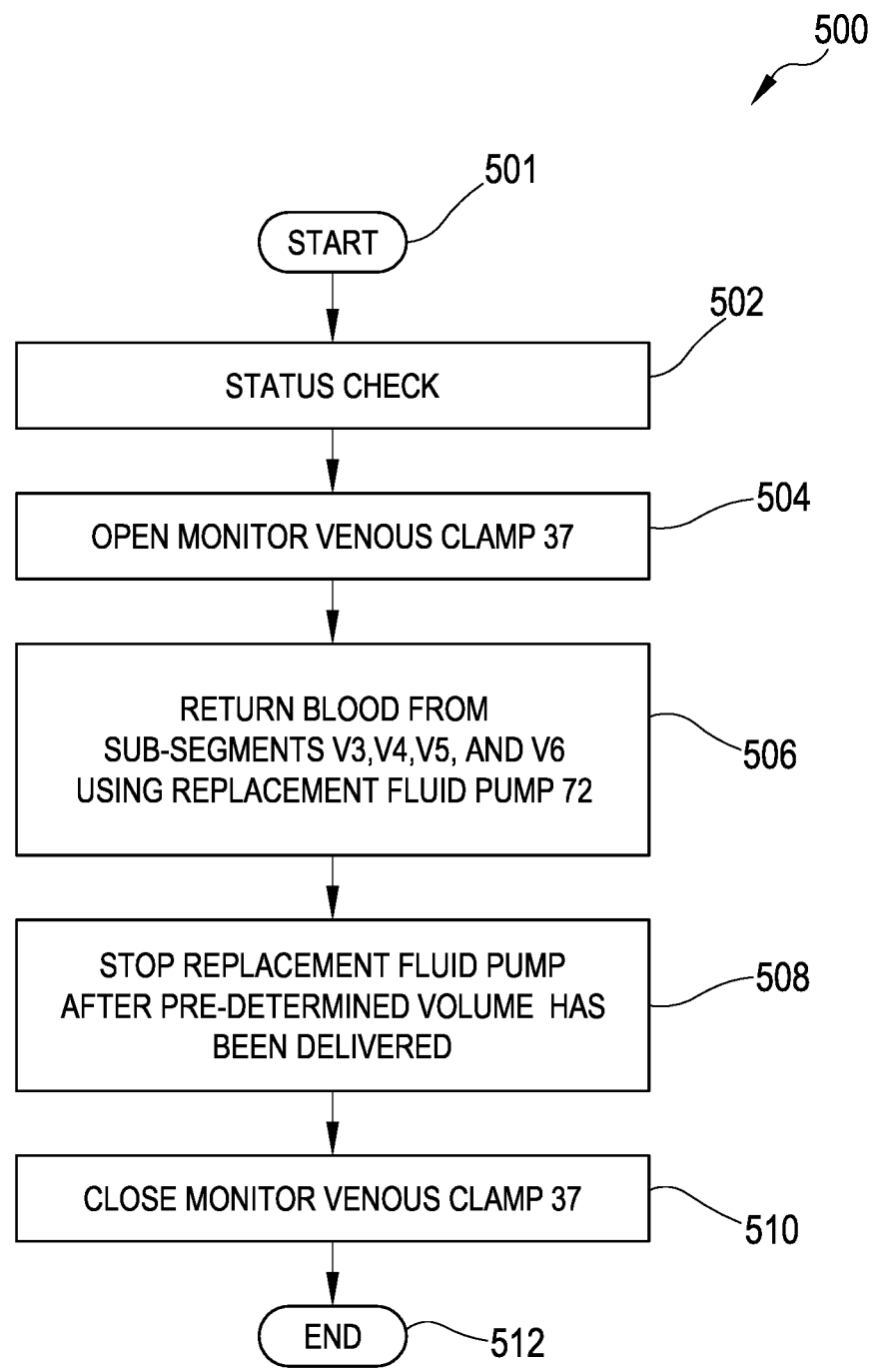
FIG. 6 shows a flow chart of a process for rinsing back blood from an extracorporeal blood circuit to a patient in accordance with a fifth embodiment of the present invention.
Figure 7:
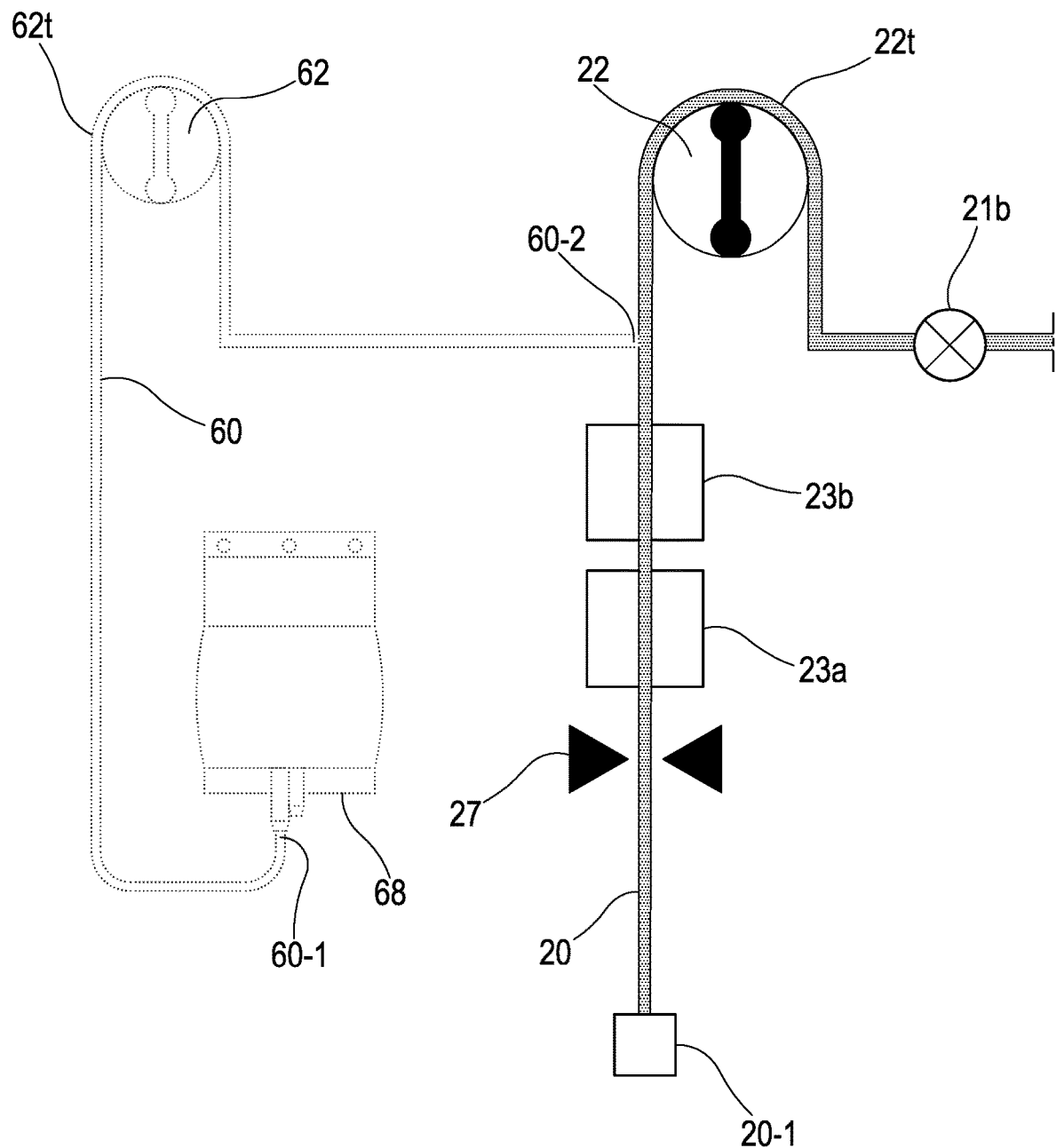
FIG. 7 schematically represents a portion of the extracorporeal blood treatment apparatus in accordance with embodiments of the present invention.

FIG. 5A shows a flow chart of a process for rinsing back blood from an extracorporeal blood circuit to a patient in accordance with a fourth embodiment of the present invention. Blood return process 400 generally includes rinsing back blood to a patient through both the blood return line 30 and the blood removal line 20 only using fluid from the replacement fluid container 78. Blood return process 400 is described with reference to FIGS. 5B, 5C, and 5D. FIG. 5B schematically illustrates a first phase (see, in particular, step 404 in FIG. 5A) of the process 400 for rinsing back blood from an extracorporeal blood circuit to a patient in accordance with the fourth embodiment of the present invention. FIG. 5C schematically illustrates a second phase (see, in particular, step 408 in FIG. 5A) of the process 400 for rinsing back blood from an extracorporeal blood circuit to a patient in accordance with the fourth embodiment of the present invention. FIG. 5D schematically illustrates a third phase (see, in particular, step 410 in FIG. 5A) of the process 400 for rinsing back blood from an extracorporeal blood circuit to a patient in accordance with the fourth embodiment of the present invention. Blood return process 400 starts at step 401 and blood pump is stopped. In step 402, the requirements for performing process 400 are evaluated in a status check. This may include making sure that the fluid volume present in the replacement fluid container 78 is greater than $\alpha*(V1+V2+V3+V4+V5+V6+V_{33})$, with a being set at a desired limit (e.g. up to 1.0). The blood return in process 400 is performed through both the blood removal line 20 and the blood return line 30. The fluid volume returned through the blood removal line 20 (i.e. on the access side) is $\alpha^*(V1+V2)$ and the fluid volume returned through the blood return line (i.e. on the venous side) is $\alpha^*(V3+V4+V5+V6+V_{33})$. If the requirements are not met, in particular if the volume present in the replacement fluid container 78 is not greater than $\alpha^*(V1+V2+V3+V4+V5+V6+V_{33})$, process 400 may still be performed in order to rinse back at least some of the blood present in the blood circuit (see above). Again, in some cases, minimum requirements may be defined, which determine whether the rinseback procedure 400 is fully, partially, or not at all performed. If the requirements are met the blood pump 22 is controlled, in step 404, to move a pre-determined volume of blood towards and through the treatment unit 10 as shown in FIG. 5B (in this specific case, the arterial clamp 27 is open, meaning that some blood is still withdrawn from the patient vascular access. The pre-determined volume of blood being returned serves to convey blood downstream from the first pre-infusion site 20-3b, which may contain gas or air (e.g. coming from the PBP solution) and typically is about 1.5 to 2.0*(V1+V2). For process 400 to commence, it is not necessary to close any of the blood lines, for example the blood return line 30. At step 406, after the pre-determined volume of blood has been conveyed, the blood pump 22 is stopped and the arterial clamp 27 is closed. At step 408, the replacement fluid pump 72 is controlled to return fluid downstream from the second pre-infusion site 20-3a as shown in FIG. 5C, with the blood pump 22 stopped. At step 410, after a pre-determined delay after step 408 has been initiated and in parallel to the operation of the replacement fluid pump 78, the clamp 27 is opened and the blood pump 22 is controlled to operate in reverse, thereby returning blood towards the first end 20-1 of the blood removal line 20 at a pre-determined flow rate. This pre-determined flow rate is selected to be about 50% of the flow rate at which the replacement fluid pump 72 is controlled to operate. The pre-determined delay may be selected depending on the respective volumes to be returned. According to the fourth embodiment, the pre-determined delay may range from about 3 to 10 seconds, preferably about 5 seconds. The operation of both pumps 22 and 72 in accordance with steps 408 and 410 is illustrated in FIG. 5D. The blood pump 22 is controlled at (reverse) $Q_{return}/2$ (alternatively the blood pump may be controlled at reverse less than $Q_{return}/2$, e.g. $Q_{return}/4$) and to stop (see step 412) after a first target volume has been returned through the blood removal line 20. According to the fourth embodiment, the first target volume is $\alpha^*(V1+V2)$. The volume returned may be determined either based on the rotation of the blood pump 22. The replacement fluid pump 72 is controlled at (forward) $Q_{return}$ and to stop (see step 414) after a second target volume has been returned through the blood return line 30. According to the fourth embodiment, the second target volume is $\alpha^*(V3+V4+V5+V6+V_{33})$. The volume returned may be determined either based on the rotation of the replacement fluid pump 72 and/or based on the weight of the replacement fluid container 78 (e.g. a change in weight thereof). Again, pressures in the blood removal line (i.e. access pressure) and in the blood return line (i.e. venous pressure) are monitored in order to detect an occlusion or clotting in the blood circuit. Subsequently, at step 416, the venous clamp 37 is closed and the process 400 ends at step 418. Process 400 allows for an effectiveness of about 85% for all circuits, based on $\alpha=1.0$, indicating the return volume being about equal to the blood circuit volume. Not taking into consideration any delays due to switching times potentially necessary between different process steps, the duration is largely proportional to the blood flow-rate during the initial phase of access line flushing and the flow-rate during the return phase. The duration of process 400 in an example based on a blood circuit volume of 200 ml and alpha=1 is about 3:20 minutes at a flow rate of 100 ml/min and a blood return effectiveness of 85%. Duration can be optimized by using a higher blood flow rate during initial step 404, where there is no change in patient blood volume. For example, the same blood flow rate as during treatment might be set. The blood return flow rate prescription of 100 ml/min does apply and only to steps 408 and 410. Controlling the blood pump 22 in reverse at step 410 at the pre-determined flow rate of $Q_{return}/2$ may entail a significant advantage in that air/gas potentially introduced from the replacement bag 78 along pre-infusion line 70 are, thus, more likely to be conveyed towards the treatment unit 10 and through blood return line 30, which includes an air separator 35 configured to remove any air/gas from the fluid conveyed. It is noted that the volume returned through the blood return line 30 (e.g. $V3+V4+V5+V6+V_{33}$) is normally at least 3 times higher than the volume returned through the blood removal line 20 (e.g. V2 or V1+V2). In these conditions/circumstances, it is possible to significantly decrease the flow-rate in the blood removal line 20 as low as $Q_{return}/4$ while maintaining the same duration for the entire blood return process 400. FIG. 5E schematically represents a portion of the extracorporeal blood treatment apparatus in accordance with embodiments of the present invention. With respect to process 400 above, the arrangement of blood pump 22 and sensor 21a (e.g. a pressure sensor including a pressure pod structure) may provide an additional advantage. As shown in FIG. 5E, the specific arrangement of the blood pump 22 and sensor 21a during the reverse operation of blood pump 22 may trap any (or most of) residual air/gas included in the fluid returned through blood removal line 20. Air/gas may be trapped in the region of pressure pod 21a and further at the outlet port of pump tract 22t. This further increases safety of process 400. FIG. 6 shows a flow chart of a process for rinsing back blood from an extracorporeal blood circuit to a patient in accordance with a fifth embodiment of the present invention. Blood return process 500 generally corresponds to a reduced version of above-described processes 100/200 or 400 and includes rinsing back blood to a patient through both the blood return line 30 only using fluid from the replacement fluid container 78. Process 500 may preferably be used in case no PBP fluid is available (e.g. PBP fluid container 68 is empty or not present), or if the residual volume of replacement fluid available in replacement fluid container 78 is too low (e.g. determined by weighing replacement fluid container 78 or by an air sensor in pre-infusion line 60 detecting bubbles caused by an empty container 68). Blood return process 500 is described with reference to FIG. 5C. FIG. 5C schematically illustrates step 506 of process 500 for rinsing back blood from an extracorporeal blood circuit to a patient in accordance with the fifth embodiment of the present invention. Blood return process 500 starts at step 501. In step 502, the requirements for performing process 500 are evaluated in a status check. This may include making sure that the fluid volume present in the replacement fluid container 78 is greater than $\alpha^*(V3+V4+V5+V6+V_{33})$, with a being set at a desired limit (e.g. up to 1.0). The blood return in process 500 is performed through the blood return line 30. The fluid volume returned through the blood return line (i.e. on the venous side) is $\alpha^*(V3+V4+V5+V6+V_{33})$. If the requirements are not met, in particular if the volume present in the replacement fluid container 78 is not greater than $\alpha^*(V3+V4+V5+V6+V_{33})$, process 500 may still be performed in order to rinse back at least some of the blood present in the blood circuit (see above). Again, in some cases, minimum requirements may be defined, which determine whether the rinse-back procedure 500 is fully, partially, or not at all performed. If the requirements are met the monitor venous clamp 37 is open at step 504. At step 506, the replacement fluid pump 72 is controlled to return fluid downstream from the second pre-infusion site 20-3*a* as shown in FIG. 5C. The replacement fluid pump 72 is controlled to stop (see step 508) after the target volume has been returned through the blood return line 30. According to the fifth embodiment, the target volume is $\alpha*(V3+V4+V5+V6+V_{33})$. The volume returned may be determined either based on the rotation of the replacement fluid pump 72 and/or based on the weight of the replacement fluid container 78 (e.g. a change in weight thereof). Again, pressure in the blood return line (i.e. venous pressure) is monitored in order to detect an occlusion or clotting in the blood circuit. Subsequently, at step 510, the venous clamp 37 is closed and process 500 ends at step 512. Process 500 allows for an effectiveness of about 77/82/87% for LF set/HF set/HF set with blood warmer sets (see above). For $\alpha=1.0$ the theoretical effectiveness is about 85% and the actual effectiveness of return process 500 is about 65/69/74% for LF set/HF set/HF set with blood warmer. The duration of process 500 is proportional to the return flow rate. The duration of process 500 in an example based on an adult set including a blood warmer is about 2:20 minutes at a flow rate of 100 ml/min and a blood return effectiveness of 74%. FIG. 7 schematically represents a portion of the extracorporeal blood treatment apparatus in accordance with embodiments of the present invention, in particular a portion of the blood removal line 20 and PBP pre-infusion line 60. The extracorporeal blood circuit may further comprise an air bubble detector 23*b*, such as an ultrasonic air bubble detector (UABD), and/or a (e.g. ultrasonic) flow meter 23*a*, as well as a flow controller 27 (e.g. a clamp or a valve). The integration of an UABD 23*b* into the blood removal line 20 allows for the detection of air bubbles in the blood or fluid returned to the patient. This is particularly useful in combination with rinse-back procedure 400 where in step 410 blood pump 22 is operated in reverse in order to rinse back blood towards the first end 20-1 of the blood removal line 20. As can be seen in FIG. 7, sensor 23*b* is configured to detect air/gas in the fluid returned to the patient towards the first end 20-1 of the blood removal line 20 so that in case the fluid should contain detectable amounts of air/gas the flow controller 27 can be activated and the air/gas can be prevented from passing through the patient access and from entering the cardiovascular system of the patient. A further advantage includes that fluid entering the extracorporeal circuit (e.g. during regular treatment) may be monitored for air/gas so that an abnormal introduction of air/gas into the extracorporeal circuit (e.g. due to a disconnection from the patient and/or from the PBP fluid container) can be prevented. In such cases, the blood removal line may be clamped (see flow controller 27) or an alarm condition may be activated. This, in turn, may allow staff to attend to the situation (e.g. reconnect patient access) or a corresponding blood return procedure to be initiated. In accordance with a further rinse-back procedure, also a medical fluid (e.g. fresh dialysis fluid) from dialysis fluid container 48 may be used. In particular, the control unit (80) checks whether there is sufficient fluid in the dialysis fluid container 48 to at least push the extracorporeal blood volume contained in the extracorporeal blood circuit downstream the post-infusion line injection point. If fluid is available, the blood pump is stopped (and arterial clamp 27 is closed). The dialysate pump 42 is activated and blood pushed back into the patient. In addition, particularly in case an air bubble detector is present in the blood removal line 20 (see FIG. 7) and enough dialysis fluid is in the dialysate container 48, the blood pump 22 may be activated in reverse pumping to pump blood towards the patient access (first end 20-1 of blood removal line 20). Arterial clamp 27 should be open and venous clamp 37 closed. Additionally dialysate pump 42 is to be activated and synchronized with blood pump 22. When target of restituted blood is achieved (or dialysis fluid in the dialysate container substantially terminated), the process is stopped. Clearly, the air bubble detector 23*b* verifies that no air is returned to the patient and the control unit 80 blocks the rinse-back in case air is detected. It is worth to note that the medical fluid contained in the dialysate container may be used to have further fluid available during any of the previously described embodiment in case the fluid contained in either (or both) the pre-infusion container 68 or the replacement container 78 is not sufficient for completely restitute the extracorporeal blood. In such a case, instead of terminating the described procedures, a further rinse-back step may be added making use of the dialysis fluid when infused in post dilution.

For example, in the second embodiment, once all maximum fluid from the pre-infusion container 68 has been used and in case blood is still in the extracorporeal blood circuit, the post-infusion line may be used to push back the blood still in the final portion of the blood return line downstream the post-infusion injection point. The same additional step may be performed in the third embodiment, once all maximum fluid from the pre-infusion container 68 has been used and in case blood is still in the extracorporeal blood circuit. As to blood return prescription, the description focused on the possibility to select a parameter value, e.g. from 0.75 to 1). However, the prescription values in each of the described embodiments might be entered as fluid volumes expressed as, e.g.

a ratio to circuit blood volume ($\beta$); or a volume to be returned (Vreturn).

Referring for example to the first embodiment, the prescription would have been modified to: PBP fluid volume staying at value V2 and replacement fluid volume=$\beta*V_{total}-V2$, wherein $V_{total}$ is the total blood circuit volume, namely $V1+V2+V3+V4+V5+V6+V_{33}$. As a further alternative, the operator may set flow rates as blood return prescription, and the apparatus checks fluid availability an proper (optimized) rinse-back procedure based on pre-set values.

In the previous description, sensors for determining the fluid content in the various containers have been described and used to determine the proper fluid availability. However, the present invention is not limited to the presence and use of such sensors (e.g. scales). Indeed, in the case of volumetric systems (e.g. with no scales) and in a configuration where the system cannot automatically evaluate available fluid volumes (typically the case of volumetric systems with no information on container sizes), the operator might be prompted to confirm/assess available volumes (as status check) in either or both pre-infusion container, replacement container and dialysate container. Blood return process is kept unchanged with the addition of possible interruptions/re-routing in case an empty bag signal occur (e.g. from an air detector in the fluid circuit). While the invention has been described in connection with what is presently considered to be the most practical and preferred embodiment, it is to be understood that the invention is not to be limited to the disclosed embodiment, but on the contrary, is intended to cover various modifications and equivalent arrangements included within the scope of the appended claims.

The invention claimed is:

1. An apparatus for continuous renal replacement therapy comprising:
- a blood circuit comprising a blood removal line, a treatment unit, and a blood return line, the blood treatment unit comprising a semipermeable membrane, a first chamber, and a second chamber, the semipermeable membrane being configured for separating the first chamber from the second chamber, the blood removal line having a first end destined to be connected to a vascular system of a subject and a second end connected to an inlet port of the first chamber, the blood return line having a first end connected to an outlet port of the first chamber and a second end destined to be connected to the vascular system;
- a replacement fluid container configured for containing a medical fluid;
- an infusion line having a first end connected to the replacement fluid container and a second end connected to the blood circuit;
- a blood pump active on the blood circuit;
- a replacement fluid pump active on the pre-infusion line;
- a second pre-infusion line;
- a pre-blood pump (PBP) connected to the control unit and active on the second pre-infusion line;
- a PBP fluid container configured for containing a second medical fluid; wherein the second pre-infusion line has a first end connected to the PBP fluid container and a second end connected to the blood removal line, the second end of the second pre-infusion line being connected to the blood removal line downstream from the first end of the blood removal line and upstream from the blood pump;
- a control unit connected to the replacement fluid pump and to the blood pump and configured to operate one or both of the replacement fluid pump and the blood pump to perform a rinse-back procedure for restitution of blood to a patient at an end of treatment, the rinse-back procedure comprising conveying blood contained in the blood circuit towards the second end of the blood return line using the medical fluid;
- wherein the rinse-back procedure further comprises:
  - controlling the blood pump and the PBP to convey fluid from the PBP fluid container towards the treatment unit; and
  - controlling the blood pump and the PBP to stop conveying fluid when a first predetermined amount of fluid has been conveyed.

2. The apparatus of claim 1, wherein the rinse-back procedure comprises preventing fluid flow through the blood removal line proximate the first end of the blood removal line before conveying blood contained in the blood circuit towards the second end of the blood return line using the medical fluid.

3. The apparatus of claim 1, wherein the second end of the pre-infusion line is connected to the blood removal line at a pre-infusion site located downstream from the blood pump and upstream from the second end of the blood removal line.

4. The apparatus of claim 1, wherein the rinse-back procedure comprises:
- blocking a fluid flow towards a first end of the blood removal line;
- enabling fluid flow through the blood return line;
- controlling the replacement fluid pump to convey fluid at a first flow rate from the replacement fluid container towards the treatment unit;
- controlling the replacement fluid pump to stop conveying fluid when a second predetermined amount of fluid has been conveyed; and
- disabling fluid flow through the blood return line.

5. The apparatus of claim 1, further comprising a PBP fluid sensor connected to the control unit and configured to generate a PBP fluid signal indicative of an amount of PBP fluid present in the PBP fluid container, wherein the control unit is further configured to determine, based on changes of the PBP fluid signal over time, a PBP flow rate signal indicative of a flow rate of PBP fluid flowing from the PBP fluid container.

6. The apparatus of claim 1, wherein the rinse-back procedure comprises conveying blood contained in the blood circuit towards the second end of the blood return line using the medical fluid of the replacement fluid container and the second medical fluid of a PBP fluid container, while fluid flow through the blood removal line is being prevented.

7. The apparatus of claim 1, wherein the rinse-back procedure comprises:
- blocking a fluid flow towards a first end of the blood removal line;
- enabling fluid flow through the blood return line;
- controlling the replacement fluid pump to convey fluid at a first flow rate from the replacement fluid container towards the treatment unit;
- controlling the replacement fluid pump to stop conveying fluid when a second predetermined amount of fluid has been conveyed; and
- disabling fluid flow through the blood return line, wherein controlling the blood pump and the PBP to convey fluid from the PBP fluid container towards the treatment unit and controlling the blood pump and the PBP stop conveying fluid when a first predetermined amount of fluid has been conveyed are performed before controlling the replacement fluid pump to convey fluid at a first flow rate from the replacement fluid container towards the treatment unit and before controlling the replacement fluid pump to stop conveying fluid when a second predetermined amount of fluid has been conveyed.

8. The apparatus of claim 1, wherein the rinse-back procedure comprises:
- blocking fluid flow towards a first end of the blood removal line;
- enabling fluid flow through the blood return line;
- controlling the replacement fluid pump to convey fluid at a first flow rate from the replacement fluid container towards the treatment unit;
- controlling the replacement fluid pump to stop conveying fluid when a second predetermined amount of fluid has been conveyed; and
- controlling the blood pump and the PBP to convey fluid from the PBP fluid container towards the treatment unit until a total amount of fluid conveyed reaches a third predetermined amount of fluid; and
- disabling fluid flow through the blood return line,
- wherein controlling the blood pump and the PBP to convey fluid from the PBP fluid container towards the treatment unit until a total amount of fluid conveyed reaches a third predetermined amount of fluid is performed after controlling the replacement fluid pump to convey fluid at a first flow rate from the replacement fluid container towards the treatment unit and after controlling the replacement fluid pump to stop conveying fluid when a second predetermined amount of fluid has been conveyed.

9. The apparatus of claim 4, wherein the rinse-back procedure further comprises, while controlling the replacement fluid pump to convey fluid at a first flow rate from the replacement fluid container towards the treatment unit and after a predetermined pumped fluid volume with the replacement fluid pump, controlling the blood pump to convey fluid in reverse at a second flow rate towards the first end of the blood removal line, the first flow rate being higher than the second flow rate;

and wherein the rinse-back procedure comprises controlling the blood pump to stop conveying fluid when a target amount of fluid has been conveyed.

10. The apparatus of claim 9, wherein the rinse-back procedure further comprises, before blocking fluid flow towards a first end of the blood removal line:

enabling fluid flow through the blood removal line;
enabling fluid flow through the blood return line;
controlling the blood pump to convey blood towards the treatment unit after enabling fluid flow through the blood removal line and after enabling fluid flow through the blood return line; and
controlling the blood pump to stop conveying blood when a tenth predetermined amount of blood has been conveyed.

11. The apparatus of claim 4, wherein the rinse-back procedure further comprises, before enabling fluid flow through the blood return line:

prompting a user to disable fluid flow through the blood removal line; and
checking whether fluid flow through the blood removal line has been disabled.

12. The apparatus of claim 4, wherein the rinse-back procedure further comprises performing a status check including determining an amount of fluid in one or more of the PBP fluid container, a dialysate container, and the replacement fluid container.

13. The apparatus of claim 1, further comprising a first flow controller, connected to the control unit, and active on the blood removal line to prevent fluid flow in the blood removal line and a second flow controller, connected to the control unit, and active on the blood return line to prevent fluid flow in the blood return line, wherein the first and second flow controllers each include a corresponding clamp mechanism operably coupled respectively to the blood removal line and to the blood return line.

14. The apparatus of claim 1, further comprising:
an air separator arranged on the blood return line;
an air bubble detector arranged on the blood return line and placed downstream the air separator;
a dialysate container configured for containing dialysate;
a dialysate line having a first end connected to the dialysate container and another end connected to the blood return line; and
a dialysate pump connected to the control unit and active on the dialysate line.

15. The apparatus of claim 1, wherein the medical fluid includes dialysis liquid with sodium and chloride ions, and one or more of calcium ions, potassium ions and magnesium ions, the dialysis liquid being different in composition from saline solution.

16. The apparatus of claim 1, wherein the control unit is configured to store PBP flow rate during treatment and, during the rinse-back procedure, the control unit is configured to infuse less than the equivalent of 10 minutes of mean PBP flow rate.

17. An apparatus for continuous renal replacement therapy comprising:
a blood circuit comprising a blood removal line, a treatment unit, and a blood return line, the blood treatment unit comprising a semipermeable membrane, a first chamber, and a second chamber, the semipermeable membrane being configured for separating the first chamber from the second chamber, the blood removal line having a first end destined to be connected to a vascular system of a subject and a second end connected to an inlet port of the first chamber, the blood return line having a first end connected to an outlet port of the first chamber and a second end destined to be connected to the vascular system;
a replacement fluid container configured for containing a medical fluid;
an infusion line having a first end connected to the replacement fluid container and a second end connected to the blood circuit;
a blood pump active on the blood circuit;
a replacement fluid pump active on the pre-infusion line;
a control unit connected to the replacement fluid pump and to the blood pump and configured to operate one or both of the replacement fluid pump and the blood pump to perform a rinse-back procedure for restitution of blood to a patient at an end of treatment, the rinse-back procedure comprising:
monitoring an amount of fluid present in the replacement fluid container at the time of activation of the rinse-back procedure;
determining a selected rinse-back mode from a group comprising a plurality of rinse-back modes, wherein the selected rinse-back mode is determined at least based on the amount of the medical fluid present in the fluid container; and
conveying blood contained in the blood circuit towards the second end of the blood return line using the medical fluid.

18. The apparatus of claim 17, comprising a replacement fluid sensor connected to the control unit and configured to generate a replacement fluid signal indicative of an amount of replacement fluid present in the replacement fluid container, the control unit being further configured to determine, based on the replacement fluid signal, a replacement fluid amount signal indicative of an amount of replacement fluid present in the replacement fluid container, the control unit being further configured to determine, based on changes of the replacement fluid signal over time, a replacement fluid flow rate signal indicative of a flow rate of replacement fluid flowing from the replacement fluid container.

19. The apparatus of claim 17 further comprising:
a second pre-infusion line;
a pre-blood pump (PBP) connected to the control unit and active on the second pre-infusion line; and
a PBP fluid container configured for containing a second medical fluid;
wherein the second pre-infusion line has a first end connected to the PBP fluid container and a second end connected to the blood removal line;
the control unit being further configured to determine a selected rinse-back mode based on an amount of the medical fluid present in the replacement fluid container and an amount of the second medical fluid present in the PBP fluid container;

wherein the control unit is further configured to monitor an amount of fluid present in the PBP fluid container at a time of activation of the rinse-back procedure.

20. The apparatus of the preceding claim 19 further comprising a PBP fluid sensor connected to the control unit and configured to generate a PBP fluid signal indicative of an amount of PBP fluid present in the PBP fluid container, wherein the control unit is further configured to determine, based on changes of the PBP fluid signal over time, a PBP flow rate signal indicative of a flow rate of PBP fluid flowing from the PBP fluid container.

21. The apparatus of claim 19, wherein the control unit is configured to perform the rinse-back procedure according to a first mode in which the rinse-back procedure further comprises:
blocking a fluid flow towards a first end of the blood removal line;
enabling fluid flow through the blood return line;
controlling the blood pump and the PBP to convey fluid from the PBP fluid container towards the treatment unit;
controlling the blood pump and the PBP stop conveying fluid when a second predetermined amount of fluid has been conveyed;
controlling the replacement fluid pump to convey fluid from the replacement fluid container towards the treatment unit;
controlling the replacement fluid pump to stop conveying fluid when a set predetermined amount of fluid has been conveyed; and
disabling fluid flow through the blood return line.

22. The apparatus of claim 17, wherein the control unit is configured to enable the rinse-back procedure according to a first mode when an amount of fluid present in the replacement fluid container is equal to or greater than the set predetermined amount and an amount of fluid present in the PBP fluid container is equal to a second predetermined amount, the second predetermined amount being equal to $\alpha \cdot V2$;
wherein $\alpha$ is a constant value and $V2$ is a volume of the blood circuit included between a first and a second pre infusion site.

23. The apparatus of claim 19, wherein the control unit is configured to perform the rinse-back procedure according to a second mode in which the rinse-back procedure further comprises:
blocking a fluid flow towards a first end of the blood removal line;
enabling fluid flow through the blood return line;
controlling the blood pump and the PBP to convey fluid from the PBP fluid container towards the treatment unit;
controlling the blood pump and the PBP to stop conveying fluid when a second predetermined amount of fluid has been conveyed;
controlling the replacement fluid pump to convey fluid from the replacement fluid container towards the treatment unit; and
when the amount of fluid conveyed by the replacement fluid pump is less than a set predetermined amount of fluid, controlling the blood pump and the PBP to convey fluid from the PBP fluid container towards the treatment unit until a total amount of fluid conveyed reaches the set predetermined amount of fluid; and
disabling fluid flow through the blood return line.

24. The apparatus of claim 23, wherein the control unit is configured to enable the rinse-back procedure according to the second mode when an amount of fluid present in the replacement fluid container is equal to or greater than the eighth pre-determined amount and an amount of fluid present in the PBP fluid container is equal to the second predetermined amount; and
the control unit is configured to disable the rinse-back procedure according to the second mode when the amount of medical fluid present in the fluid container is less than a pre-determined minimum amount.

25. The apparatus of claim 19, wherein the control unit is configured to perform the rinse-back procedure according to a third mode in which the rinse-back procedure further comprises:
enabling fluid flow through the blood return line;
controlling the blood pump and the PBP to convey fluid from the PBP fluid container towards the treatment unit;
controlling the blood pump and the PBP stop conveying fluid when a ninth predetermined amount of fluid has been conveyed; and
disabling fluid flow through the blood return line;
wherein the control unit is configured to enable said rinse-back procedure according to the third mode when an amount of fluid present in the replacement fluid container is equal to or greater than an eighth pre-determined amount and an amount of fluid present in the PBP fluid container is equal to a second predetermined amount;
and wherein the control unit is configured to disable the rinse-back procedure according to the third mode when the amount of medical fluid present in the fluid container is less than a pre-determined minimum amount.

26. The apparatus of claim 19, wherein the control unit is configured to perform the rinse-back procedure according to a fourth mode in which the rinse-back procedure further comprises:
controlling the blood pump to convey blood towards the treatment unit;
controlling the blood pump to stop conveying blood when a tenth predetermined amount of blood has been conveyed;
controlling the replacement fluid pump to convey fluid at a first flow rate from the replacement fluid container towards the treatment unit and, after a predetermined pumped fluid volume, controlling the blood pump to convey fluid in reverse at a second flow rate towards the first end of the blood removal line, the first flow rate being higher than the second flow rate;
controlling the replacement fluid pump to stop conveying fluid when a first target amount of fluid has been conveyed and controlling the blood pump to stop conveying fluid when a second target amount of fluid has been conveyed; and
disabling fluid flow through the blood return line.

27. The apparatus of claim 19, wherein the control unit is configured to perform the rinse-back procedure according to a fifth mode in which the rinse-back procedure further comprises:
enabling fluid flow through the blood return line;
controlling the replacement fluid pump to convey fluid from the replacement fluid container towards the treatment unit;
controlling the replacement fluid pump to stop conveying fluid when a set predetermined amount of fluid has been conveyed; and
disabling fluid flow through the blood return line;

wherein the control unit is configured to enable the rinse-back procedure according to the fifth mode when an amount of fluid present in the replacement fluid container is equal to or greater than the eighth predetermined amount and an amount of fluid present in the PBP fluid container is equal to a second predetermined amount; and wherein the control unit is configured to disable the rinse-back procedure according to the fifth mode when the amount of medical fluid present in the fluid container is less than a pre-determined minimum amount.

28. The apparatus of claim 17 further comprising:
a dialysate container configured for containing dialysate;
a dialysate line having a first end connected to the dialysate container and a second end connected to an inlet port of the second chamber; and
a dialysate pump connected to the control unit and active on the dialysate line,
the apparatus further comprising a dialysate sensor connected to the control unit and configured to generate a dialysate signal indicative of an amount of dialysate present in the dialysate container.

29. The apparatus of claim 17, wherein the second end of the pre-infusion line is connected to the blood removal line at a pre-infusion site located downstream from the blood pump and upstream from the second end of the blood removal line.

30. The apparatus of claim 17, wherein the rinse-back procedures comprise conveying blood contained in the blood circuit towards the second end of the blood return line using the medical fluid of the replacement fluid container and a second medical fluid of a PBP fluid container while fluid flow through the blood removal line is being prevented.

31. The apparatus of claim 22, wherein the rinse-back procedures according to the first, second, third and fifth modes, further comprise, prior to enabling fluid flow through the blood return line:
prompting a user to disable fluid flow through the blood removal line; and
checking whether fluid flow through the blood removal line has been disabled.

32. An apparatus for continuous renal replacement therapy comprising:
a blood circuit comprising a blood removal line, a treatment unit, and a blood return line, the blood treatment unit comprising a semipermeable membrane, a first chamber, and a second chamber, the semipermeable membrane being configured for separating the first chamber from the second chamber, the blood removal line having a first end destined to be connected to a vascular system of a subject and a second end connected to an inlet port of the first chamber, the blood return line having a first end connected to an outlet port of the first chamber and a second end destined to be connected to the vascular system;
a replacement fluid container configured for containing a medical fluid;
an infusion line having a first end connected to the replacement fluid container and a second end connected to the blood circuit;
a blood pump active on the blood circuit;
a replacement fluid pump active on the pre-infusion line; and
a control unit connected to the replacement fluid pump and to the blood pump and configured to operate one or both of the replacement fluid pump and the blood pump to perform a rinse-back procedure for restitution of blood to a patient at an end of treatment, the rinse-back procedure comprising:
conveying blood contained in the blood circuit towards the second end of the blood return line using the medical fluid;
blocking a fluid flow towards a first end of the blood removal line;
enabling fluid flow through the blood return line;
controlling the replacement fluid pump to convey fluid at a first flow rate from the replacement fluid container towards the treatment unit;
controlling the replacement fluid pump to stop conveying fluid when a second predetermined amount of fluid has been conveyed; and
disabling fluid flow through the blood return line;
wherein the rinse-back procedure further comprises, while controlling the replacement fluid pump to convey fluid at a first flow rate from the replacement fluid container towards the treatment unit and after a predetermined pumped fluid volume with the replacement fluid pump, controlling the blood pump to convey fluid in reverse at a second flow rate towards the first end of the blood removal line, the first flow rate being higher than the second flow rate;
and wherein the rinse-back procedure comprises controlling the blood pump to stop conveying fluid when a target amount of fluid has been conveyed.

33. The apparatus of claim 32 further comprising:
a second pre-infusion line;
a pre-blood pump (PBP) connected to the control unit and active on the second pre-infusion line; and
a PBP fluid container configured for containing a second medical fluid; wherein the second pre-infusion line has a first end connected to the PBP fluid container and a second end connected to the blood removal line, the second end of the second pre-infusion line being connected to the blood removal line downstream from the first end of the blood removal line and upstream from the blood pump;
wherein the rinse-back procedure further comprises:
controlling the blood pump and the PBP to convey fluid from the PBP fluid container towards the treatment unit;
controlling the blood pump and the PBP stop conveying fluid when a first predetermined amount of fluid has been conveyed.

34. The apparatus of claim 32, further comprising:
a second pre-infusion line;
a pre-blood pump (PBP) connected to the control unit and active on the second pre-infusion line; and
a PBP fluid container configured for containing a citrate solution; the second pre-infusion line having a first end connected to the PBP fluid container and a second end connected to the blood removal line,
wherein the control unit is configured to store PBP flow rate during treatment and, during the rinse-back procedure, the control unit is configured to infuse less than the equivalent of 10 minutes of mean PBP flow rate.

35. The apparatus of claim 33, further comprising a PBP fluid sensor connected to the control unit and configured to generate a PBP fluid signal indicative of an amount of PBP fluid present in the PBP fluid container, wherein the control unit is further configured to determine, based on changes of the PBP fluid signal over time, a PBP flow rate signal indicative of a flow rate of PBP fluid flowing from the PBP fluid container.

36. The apparatus of claim 33, wherein the rinse-back procedure comprises conveying blood contained in the blood circuit towards the second end of the blood return line using the medical fluid of the replacement fluid container and the second medical fluid of a PBP fluid container, while fluid flow through the blood removal line is being prevented.

37. The apparatus of claim 33, wherein the rinse-back procedure comprises:
blocking a fluid flow towards a first end of the blood removal line;
enabling fluid flow through the blood return line;
controlling the replacement fluid pump to convey fluid at a first flow rate from the replacement fluid container towards the treatment unit;
controlling the replacement fluid pump to stop conveying fluid when a second predetermined amount of fluid has been conveyed; and
disabling fluid flow through the blood return line, wherein controlling the blood pump and the PBP to convey fluid from the PBP fluid container towards the treatment unit and controlling the blood pump and the PBP to stop conveying fluid when a first predetermined amount of fluid has been conveyed are performed before controlling the replacement fluid pump to convey fluid at a first flow rate from the replacement fluid container towards the treatment unit and before controlling the replacement fluid pump to stop conveying fluid when a second predetermined amount of fluid has been conveyed.

38. The apparatus of claim 33, wherein the rinse-back procedure comprises:
blocking fluid flow towards a first end of the blood removal line;
enabling fluid flow through the blood return line;
controlling the replacement fluid pump to convey fluid at a first flow rate from the replacement fluid container towards the treatment unit;
controlling the replacement fluid pump to stop conveying fluid when a second predetermined amount of fluid has been conveyed; and
controlling the blood pump and the PBP to convey fluid from the PBP fluid container towards the treatment unit until a total amount of fluid conveyed reaches a third predetermined amount of fluid; and
disabling fluid flow through the blood return line,
wherein controlling the blood pump and the PBP to convey fluid from the PBP fluid container towards the treatment unit until a total amount of fluid conveyed reaches a third predetermined amount of fluid is performed after controlling the replacement fluid pump to convey fluid at a first flow rate from the replacement fluid container towards the treatment unit and after controlling the replacement fluid pump to stop conveying fluid when a second predetermined amount of fluid has been conveyed.

39. An apparatus for continuous renal replacement therapy comprising:
a blood circuit comprising a blood removal line, a treatment unit, and a blood return line, the blood treatment unit comprising a semipermeable membrane, a first chamber, and a second chamber, the semipermeable membrane being configured for separating the first chamber from the second chamber, the blood removal line having a first end destined to be connected to a vascular system of a subject and a second end connected to an inlet port of the first chamber, the blood return line having a first end connected to an outlet port of the first chamber and a second end destined to be connected to the vascular system;
a replacement fluid container configured for containing a medical fluid;
an infusion line having a first end connected to the replacement fluid container and a second end connected to the blood circuit;
a blood pump active on the blood circuit;
a replacement fluid pump active on the pre-infusion line; and
a control unit connected to the replacement fluid pump and to the blood pump and configured to operate one or both of the replacement fluid pump and the blood pump to perform a rinse-back procedure for restitution of blood to a patient at an end of treatment, the rinse-back procedure comprising:
conveying blood contained in the blood circuit towards the second end of the blood return line using the medical fluid;
blocking a fluid flow towards a first end of the blood removal line;
enabling fluid flow through the blood return line;
controlling the replacement fluid pump to convey fluid at a first flow rate from the replacement fluid container towards the treatment unit;
controlling the replacement fluid pump to stop conveying fluid when a second predetermined amount of fluid has been conveyed; and
disabling fluid flow through the blood return line;
wherein the rinse-back procedure further comprises performing a status check including determining an amount of fluid in one or more of a PBP fluid container, a dialysate container, and the replacement fluid container.

40. An apparatus for continuous renal replacement therapy comprising:
a blood circuit comprising a blood removal line, a treatment unit, and a blood return line, the blood treatment unit comprising a semipermeable membrane, a first chamber, and a second chamber, the semipermeable membrane being configured for separating the first chamber from the second chamber, the blood removal line having a first end destined to be connected to a vascular system of a subject and a second end connected to an inlet port of the first chamber, the blood return line having a first end connected to an outlet port of the first chamber and a second end destined to be connected to the vascular system;
a replacement fluid container configured for containing a medical fluid;
an infusion line having a first end connected to the replacement fluid container and a second end connected to the blood circuit;
a blood pump active on the blood circuit;
a replacement fluid pump active on the pre-infusion line;
a second pre-infusion line;
a pre-blood pump (PBP) connected to the control unit and active on the second pre-infusion line;
a PBP fluid container configured for containing a citrate solution; the second pre-infusion line having a first end connected to the PBP fluid container and a second end connected to the blood removal line, and
a control unit connected to the replacement fluid pump and to the blood pump and configured to operate one or both of the replacement fluid pump and the blood pump to perform a rinse-back procedure for restitution of blood to a patient at an end of treatment, the rinse-back procedure comprising conveying blood contained in the blood circuit towards the second end of the blood return line using the medical fluid, wherein the control unit is configured to store PBP flow rate during treatment and, during the rinse-back procedure, the control unit is configured to infuse less than the equivalent of 10 minutes of mean PBP flow rate.

41. The apparatus of claim 40, wherein the rinse-back procedure comprises:

blocking a fluid flow towards a first end of the blood removal line;

enabling fluid flow through the blood return line;

controlling the replacement fluid pump to convey fluid at a first flow rate from the replacement fluid container towards the treatment unit;

controlling the replacement fluid pump to stop conveying fluid when a second predetermined amount of fluid has been conveyed; and disabling fluid flow through the blood return line, wherein the rinse-back procedure further comprises, while controlling the replacement fluid pump to convey fluid at a first flow rate from the replacement fluid container towards the treatment unit and after a predetermined pumped fluid volume with the replacement fluid pump, controlling the blood pump to convey fluid in reverse at a second flow rate towards the first end of the blood removal line, the first flow rate being higher than the second flow rate;

and wherein the rinse-back procedure comprises controlling the blood pump to stop conveying fluid when a target amount of fluid has been conveyed.

* * * * *

UNITED STATES PATENT AND TRADEMARK OFFICE
CERTIFICATE OF CORRECTION

| | | |
|---|---|---|
| PATENT NO. | : 11,951,295 B2 | Page 1 of 1 |
| APPLICATION NO. | : 16/957889 | |
| DATED | : April 9, 2024 | |
| INVENTOR(S) | : Thierry Court and Dominique Pouchoulin | |

It is certified that error appears in the above-identified patent and that said Letters Patent is hereby corrected as shown below:

In the Claims

In Column 34, Line 37, Claim 6, "the PBP stop" should be --the PBP to stop--

In Column 37, Line 22, Claim 21, "the PBP stop" should be --the PBP to stop--

In Column 38, Line 19, Claim 25, "the PBP stop" should be --the PBP to stop--

In Column 40, Line 45, Claim 33, "the PBP stop" should be --the PBP to stop--

Signed and Sealed this
First Day of October, 2024

Katherine Kelly Vidal
*Director of the United States Patent and Trademark Office*